(12) United States Patent
Brenner

(10) Patent No.: US 7,635,566 B2
(45) Date of Patent: Dec. 22, 2009

(54) METHODS AND COMPOSITIONS FOR ISOLATING NUCLEIC ACID SEQUENCE VARIANTS

(75) Inventor: Sydney Brenner, Ely (GB)

(73) Assignee: Population Genetics Technologies Ltd., Cambridge (GB)

( * ) Notice: Subject to any disclaimer, the term of this patent is extended or adjusted under 35 U.S.C. 154(b) by 0 days.

(21) Appl. No.: 12/163,571

(22) Filed: Jun. 27, 2008

(65) Prior Publication Data

US 2009/0004665 A1  Jan. 1, 2009

Related U.S. Application Data

(60) Provisional application No. 60/947,109, filed on Jun. 29, 2007.

(51) Int. Cl.
   C12Q 1/68 (2006.01)
   C07H 21/00 (2006.01)
   C07H 21/02 (2006.01)
   C07H 21/04 (2006.01)

(52) U.S. Cl. .......................... 435/6; 536/22.1; 536/23.1; 536/24.3

(58) Field of Classification Search ............. 435/6; 536/22.1, 23.1, 24.3
   See application file for complete search history.

(56) References Cited

U.S. PATENT DOCUMENTS

| | | | | |
|---|---|---|---|---|
| 5,604,097 A | * | 2/1997 | Brenner | 506/3 |
| 5,635,400 A | * | 6/1997 | Brenner | 506/41 |
| 5,654,413 A | * | 8/1997 | Brenner | 506/41 |
| 5,763,175 A | * | 6/1998 | Brenner | 435/6 |
| 5,780,231 A | * | 7/1998 | Brenner | 435/6 |
| 5,846,719 A | * | 12/1998 | Brenner et al. | 506/3 |
| 5,863,722 A | * | 1/1999 | Brenner | 435/6 |

(Continued)

FOREIGN PATENT DOCUMENTS

EP   0969103   1/2000

(Continued)

OTHER PUBLICATIONS

Till et al. High-throughput discovery of rare human nucleotide polymorphisms by Ecotilling. Nucleic Acids Research 34(13) : e99/1-e99/12 (2006).*

(Continued)

*Primary Examiner*—Ethan Whisenant
(74) *Attorney, Agent, or Firm*—David C. Scherer; Bozicevic, Field & Francis LLP

(57) ABSTRACT

The invention is drawn to isolating sequence variants of a genetic locus of interest using a modified iterative primer extension method. The nucleic acids analyzed are generally single stranded and have a reference sequence which is used as a basis for performing iterative single nucleotide extension reactions from a hybridized polymerization primer. The iterative polymerization reactions are configured such that polymerization of the strand will continue if the sequence of the nucleic acid being analyzed matches the reference sequence, whereas polymerization will be terminated if the nucleic acid being analyzed does not match the reference sequence. Nucleic acid strands that have mutations can be isolated using a variety of methods and sequenced to determine the precise identity of the mutation/polymorphism. By performing the method on both strands of the nucleic acid being analyzed, virtually all possible mutations can be identified.

20 Claims, 10 Drawing Sheets

U.S. PATENT DOCUMENTS

| | | | | |
|---|---|---|---|---|
| 5,888,737 | A * | 3/1999 | DuBridge et al. | 435/6 |
| 5,962,228 | A * | 10/1999 | Brenner | 435/6 |
| 6,013,445 | A * | 1/2000 | Albrecht et al. | 435/6 |
| 6,103,463 | A * | 8/2000 | Chetverin et al. | 435/6 |
| 6,138,077 | A * | 10/2000 | Brenner | 702/19 |
| 6,140,489 | A * | 10/2000 | Brenner | 536/24.3 |
| 6,150,516 | A * | 11/2000 | Brenner et al. | 506/3 |
| 6,172,218 | B1 * | 1/2001 | Brenner | 506/16 |
| 6,175,002 | B1 * | 1/2001 | DuBridge et al. | 536/23.1 |
| 6,228,589 | B1 * | 5/2001 | Brenner | 506/3 |
| 6,235,475 | B1 * | 5/2001 | Brenner et al. | 506/41 |
| 6,265,163 | B1 * | 7/2001 | Albrecht et al. | 435/6 |
| 6,322,971 | B1 * | 11/2001 | Chetverin et al. | 435/6 |
| 6,352,828 | B1 * | 3/2002 | Brenner | 506/3 |
| 6,406,848 | B1 * | 6/2002 | Bridgham et al. | 435/6 |
| 6,511,802 | B1 * | 1/2003 | Albrecht et al. | 506/12 |
| 6,518,023 | B1 * | 2/2003 | Brenner | 435/6 |
| 6,654,505 | B2 * | 11/2003 | Bridgham et al. | 382/278 |
| 6,806,052 | B2 * | 10/2004 | Bridgham et al. | 435/6 |
| 6,831,994 | B2 * | 12/2004 | Bridgham et al. | 382/133 |
| 6,893,822 | B2 * | 5/2005 | Schweitzer et al. | 435/6 |
| 6,897,023 | B2 * | 5/2005 | Fu et al. | 435/6 |
| 6,969,488 | B2 * | 11/2005 | Bridgham et al. | 422/61 |
| 7,090,804 | B2 * | 8/2006 | Kayyem et al. | 422/68.1 |
| 7,282,370 | B2 * | 10/2007 | Bridgham et al. | 436/172 |
| 7,390,632 | B2 * | 6/2008 | Maihle et al. | 435/7.92 |
| 2002/0051992 | A1 * | 5/2002 | Bridgham et al. | 435/6 |
| 2002/0061529 | A1 * | 5/2002 | Bridgham et al. | 435/6 |
| 2002/0137052 | A1 * | 9/2002 | Bridgham et al. | 435/6 |
| 2003/0027157 | A1 * | 2/2003 | Fu et al. | 435/6 |
| 2003/0032020 | A1 * | 2/2003 | Brenner | 435/6 |
| 2003/0049616 | A1 * | 3/2003 | Brenner et al. | 435/6 |
| 2003/0077615 | A1 * | 4/2003 | Bridgham et al. | 435/6 |
| 2003/0175702 | A1 * | 9/2003 | Schweitzer et al. | 435/6 |
| 2004/0002104 | A1 * | 1/2004 | Fischer et al. | 435/6 |
| 2004/0091857 | A1 * | 5/2004 | Nallur et al. | 435/6 |
| 2005/0059065 | A1 * | 3/2005 | Brenner | 435/6 |
| 2005/0176035 | A1 * | 8/2005 | Crothers | 435/6 |
| 2005/0181408 | A1 * | 8/2005 | Brenner | 435/6 |
| 2005/0186590 | A1 * | 8/2005 | Crothers et al. | 435/6 |
| 2005/0208576 | A1 * | 9/2005 | Schweitzer et al. | 435/6 |
| 2006/0051876 | A1 * | 3/2006 | Bridgham et al. | 436/164 |
| 2007/0219367 | A1 * | 9/2007 | Shchepinov et al. | 536/25.32 |
| 2008/0318796 | A1 * | 12/2008 | Drmanac et al. | 506/3 |

FOREIGN PATENT DOCUMENTS

| | | | |
|---|---|---|---|
| EP | 1693469 | | 8/2006 |
| WO | WO96/12039 | * | 4/1996 |
| WO | WO/96/41011 | * | 12/1996 |
| WO | 99009211 | | 2/1999 |
| WO | WO99/35293 | * | 7/1999 |
| WO | WO02/103011 | * | 12/2002 |
| WO | WO03/008638 | * | 1/2003 |
| WO | WO2005/080604 | * | 9/2005 |
| WO | 2005111244 | | 11/2005 |
| WO | WO2006/086209 | * | 8/2006 |

OTHER PUBLICATIONS

Gerry et al., Universal DNA Microarray Method for Multiplex Detection of Low Abundance Point Mutations Journal of Molecular Biology 292(2) : 251-262 (1999).*

Brenner et al. , In vitro cloning of complex mixtures of DNA on microbeads: physical separation of differentially expressed cDNAs. PNAS 97(4) : 1665-1670(2000).*

* cited by examiner

A.  5'- G A$_m$ T C Y G A$_m$ T C ---- G A$_m$ T C ---- R
         R C T A$_m$ G ---- C T A$_m$ G ---- Y C T A$_m$ G - 5'

| W (Watson) | muts | C (Crick) | muts | ~C muts | (W + ~C) muts |
|---|---|---|---|---|---|
| A | G> T> | T | ... | ... | ... |
| C | G> A> | G | C> A> | G> T> | G> A> T> |
| T | G> C> | A | C> T> | G> A> | G> C> A> |
| A | T> C> | T | G> T> | C> A> | C> T> A> |
| G | G> A> | C | G> A> | C> T> | T> A> C> |
| C | G> A> | G | T> A> | A> T> | G> A> T> |
| T | ... | A | T> C> | ... | ... |

| WT | mut1 | mut2 | mut3 |
|---|---|---|---|
| A A | A A | A A | A A |
| G G! | G G! | G G! | G G! |
| T | C | A | G |
| G | G | G | G |
| C | C | C | C |

B

| WT | mut1 | mut2 | mut3 |
|---|---|---|---|
| A A | A A | A A | A A |
| G G | G G | G G | G G |
| T T! | C C> | A A> | G G |
| G | G | G | G G |
| C | C | C | C C> |

FIG. 4

| A | WT | | mut 1 | |
|---|---|---|---|---|
| ↓ | A | A | A | A |
| | G | G! | G | G! |
| | T | | G | |
| | G | | G | |
| | T | | T | |
| | G | | G | |
| | C | | C | |

| B | WT | | mut 1 | |
|---|---|---|---|---|
| ↓ | A | A | A | A |
| | G | G | G | G |
| | T | T! | G | G |
| | G | | G | |
| | T | | T | T! |
| | G | | G | |
| | C | | C | |

| C | WT | | mut 1 | |
|---|---|---|---|---|
| ↓ | A | A | A | A |
| | G | G | G | G |
| | T | T | G | G |
| | G | G! | G | G |
| | T | | T | T |
| | G | | G | G! |
| | C | | C | C |

| D | WT | | mut 1 | |
|---|---|---|---|---|
| ↓ | A | A | A | A |
| | G | G | G | G |
| | T | G | G | G |
| | G | G | G | G |
| | T | T! | T | T |
| | G | | G | G |
| | C | | C | C> |

FIG. 5

| A | WT | | mut 1 | | mut 2 | | mut 3 | | mut 4 | |
|---|---|---|---|---|---|---|---|---|---|---|
| ↓ | T | T | T | T | T | T | T | T | T | T |
|  | G | G | A | A! | G | G | G | G | G | G |
|  | G | G | G |  | A | A! | G | G | G | G |
|  | G | G | G |  | G |  | A | A! | G | G |
|  | G | G | G |  | G |  | G |  | A | A! |
|  | A | A! | A |  | A |  | A |  | A |  |
|  | C | C | C |  | C |  | C |  | C |  |

| B | WT | | mut 1 | | mut 2 | | mut 3 | | mut 4 | |
|---|---|---|---|---|---|---|---|---|---|---|
| ↓ | T | T | T | T | T | T | T | T | T | T |
|  | G | G | A | A | G | G | G | G | G | G |
|  | G | G | G | G> | A | A | G | G | G | G |
|  | G | G | G |  | G | G> | A | A | G | G |
|  | G | G | G |  | G |  | G | G> | A | A |
|  | A | A | A |  | A |  | A |  | A | A |
|  | C | C! | C |  | C |  | C |  | C | C! |

Primer:    5' - ... C T T T T
Template:  3' - ... G A A A A C G T ... - 5'

B

Primer:    5' - ... C T T T T
Template:  3' - ... G A A A A A C G T ... - 5'

FIG. 7

METHODS AND COMPOSITIONS FOR ISOLATING NUCLEIC ACID SEQUENCE VARIANTS

BACKGROUND

There is great interest in determining nucleic acid sequences and sequence differences rapidly and efficiently for addressing a host of important problems in the biomedical sciences, e.g. Collins et al, Nature, 422: 835-847 (2003); National Cancer Institute, Report of Working Group on Biomedical Technology, "Recommendation for a Human Cancer Genome Project," (February, 2005). Not only are such measurements crucial for understanding the genetic basis of inherited traits, such as disease susceptibilities, but they are also crucial for understanding the role of somatic mutations in cancer. Many techniques have been developed and successfully applied to problems in these areas, e.g. Stephens et al, Nature Genetics, 37: 590-592 (2005); Syvanen, Nature Reviews Genetics, 2: 930-942 (2002); Kennedy et al, Nature Biotechnology, 21: 1233-1237 (2003); Hardenbol et al, Genome Research, 15: 269-275 (2005); Gunderson et al, Nature Genetics, 37: 549-554 (2005); Margulies et al, Nature, 437: 376-380 (2005); and the like. However, there are still many problems, such as the rapid and efficient discovery of genetic or epigenetic variation, that are not adequately addressed by current techniques.

The availability of a convenient and efficient method for isolating nucleic acids that vary from a reference sequence would lead to improvements in analytical assays in many fields, including scientific and biomedical research, medicine, and other industrial areas where genetic measurements are important.

SUMMARY OF THE INVENTION

The present invention provides methods and compositions for isolating one or more nucleic acids that have a sequence different from a reference sequence at a locus of interest (also called variant or mutant nucleic acids). In certain aspects, the invention employs an iterative base-by-base primer extension method to isolate variant nucleic acids from non-variant nucleic acids in a nucleic acid sample. In certain embodiments, the nucleic acid sample contains a mixture of nucleic acids from different sources (or individuals), where any source having a nucleotide sequence different from a reference sequence for the locus of interest is identified.

Aspects of the present invention include methods of isolating nucleic acid molecules from a sample having a nucleotide sequence different from a reference sequence for a locus of interest, the method including the steps of:

(i) providing a sample comprising nucleic acid molecules having a locus of interest;

(ii) annealing a polymerization primer to the nucleic acid molecules immediately upstream of the locus of interest;

(iii) contacting the polymerization primer-annealed nucleic acid molecules with a polymerization reagent pool under nucleic acid polymerization conditions, wherein the polymerization reagent pool comprises a nucleotide polymerase and two or more nucleotide bases, wherein the two or more nucleotide bases are selected based on the identity of the next two different nucleotide bases predicted to be incorporated at unoccupied sites downstream of the polymerization primer as determined by a reference sequence for the locus of interest; and (iv) isolating nucleic acid molecules in which the two or more nucleotides have not been incorporated as predicted based on the reference sequence for the locus of interest, thereby isolating nucleic acid molecules having a nucleotide sequence different from the reference sequence in the locus of interest.

In certain embodiments, the sample comprises nucleic acids from a plurality of subjects.

In certain embodiments, the subjects are mammals.

In certain embodiments, the mammals are humans.

In certain embodiments, the nucleic acids from the plurality of subjects are each tagged with a unique nucleotide tag (e.g., one or more sequence tokens).

In certain embodiments, the method further comprises determining from which of the plurality of subjects the isolated nucleic acid is derived based on the unique nucleotide tag (decoding).

In certain embodiments, the method further comprises one or both of: sub-cloning the isolated nucleic acid molecules into a vector and sequencing the isolated nucleic acid molecules.

In certain embodiments, the differences are identified in two or more of the plurality of subjects.

In certain embodiments, the differences comprise distinct polymorphisms.

In certain embodiments, the locus of interest has more than one reference sequence.

In certain embodiments, each of the polymerization reagent pool includes: a deoxyribonucleotide and two dideoxyribonucleotides.

In certain embodiments, the deoxyribonucleotide is predicted to be added in the next position of the polymerizing nucleic acid strand based on the reference sequence and the two dideoxyribonucleotides are predicted not to be added to the polymerizing strand in the next two positions of nucleic acid polymerization based on the reference sequence.

In certain embodiments, the dideoxyribonucleotides are each labeled with a distinguishing detectable label.

In certain embodiments, the detectable label is a fluorescent label.

In certain embodiments, the method further comprises:
screening the isolated nucleic acid molecules for the presence of the distinguishing detectable labels; and
determining how the sequence of the isolated nucleic acid molecules differs from the reference sequence based on the screening.

In certain embodiments, the dideoxyribonucleotides are labeled with a first member of a binding pair (e.g., biotin).

In certain embodiments, the first member of the binding pair is biotin.

In certain embodiments, the isolating step comprises contacting the sample to a second member of the binding pair (e.g., avidin, streptavidin).

In certain embodiments, the method includes sequencing the isolated nucleic acid molecules.

In certain embodiments, the polymerization primer is immobilized on a substrate.

In certain embodiments, the nucleic acid molecules are immobilized on a substrate.

In certain embodiments, the method further comprises capturing the nucleic acid molecules by hybridization to a capture primer immobilized on a substrate, wherein the capture primer binds to the same strand of the nucleic acid molecules as the polymerization primer at a location that is downstream of the polymerization primer.

In certain embodiments, the isolation step further comprises:

contacting the sample under polymerization conditions to a polymerization reagent pool comprising all four deoxyribonucleic acid triphosphates and a strand displacing nucleotide polymerase; and isolating nucleic acid molecules bound to the substrate-immobilized capture primer after the contacting step and/or isolating the nucleic acid molecules eluted from the substrate-immobilized capture primer.

In certain embodiments, the method further comprises repeating step (iii) for a predetermined number of cycles.

In certain embodiments, the isolating step is performed in each of the predetermined number of cycles.

In certain embodiments, the isolating step is performed after completion of all of the predetermined number of cycles.

In certain embodiments, the isolated nucleic acid molecules have previously unknown nucleic acid sequence differences from the reference sequence.

In certain embodiments, multiple nucleic acid molecules having distinct nucleic acid differences from the reference sequence are isolated.

Aspects of the invention include methods of eluting a nucleic acid from a substrate, the method including:

(i) obtaining a nucleic acid immobilized on a substrate via hybridization to a capture primer attached to the substrate;

(ii) annealing a polymerization primer to the immobilized nucleic acid, wherein the polymerization primer hybridizes upstream of the capture primer; and (iii) contacting the polymerization primer-annealed immobilized nucleic acid to a strand-displacing nucleotide polymerase under nucleic acid polymerization conditions;

wherein the strand displacing nucleotide polymerase displaces the capture primer from the nucleic acid, thereby eluting the nucleic acid from the substrate.

Aspects of the invention include methods of sorting nucleic acid molecules according to the identity of their corresponding unique nucleotide tags, including the steps of:

(i) contacting a nucleic acid sample comprising at least two nucleic acid molecules each having a unique tag to a first oligonucleotide primer under hybridization conditions, wherein the first oligonucleotide primer is immobilized on a substrate and contains a sequence complementary to a first region present in the at least two nucleic acid molecules, whereby the at least two nucleic acid molecules are immobilized;

(ii) contacting the immobilized at least two nucleic acid molecules to a second oligonucleotide primer under hybridization conditions, wherein the second primer contains a sequence that is complementary to a region in the unique tag of a first of the at least two nucleic acid molecules, wherein the second primer binds to the same strand as the first primer at a location that is 5' (upstream) to the first primer; and (iii) isolating the first of the at least two nucleic acid molecules by contacting the immobilized at least two nucleic acid molecules to a displacing nucleotide polymerase under nucleic acid polymerization conditions, wherein extension of the second primer displaces the first of the at least two nucleic acid molecules from the first immobilized primer;

wherein the at least two uniquely-tagged nucleic acid molecules are sorted according to the identity of their corresponding unique nucleotide tags.

In certain embodiments, the method further comprises isolating a second of the at least two nucleic acid molecules by repeating steps (ii) and (iii) using a third oligonucleotide primer, wherein the third primer comprises a sequence complementary to a region in the unique tag of a second of the at least two nucleic acid molecules, wherein the third primer binds to the same strand as the first primer at a location that is 5' (upstream) to the first primer.

Aspects of the invention include a polymerization reagent pool set containing a plurality of polymerization reagent pools, wherein each of the plurality of polymerization reagent pools includes:

(i) a nucleotide polymerase;

(ii) a deoxyribonucleotide base; and (iii) a dideoxyribonucleotides nucleotide base different from the deoxyribonucleotide base;

wherein each of the plurality of polymerization reagent pools has a unique combination of the deoxyribonucleotide and the dideoxyribonucleotide base, and wherein the polymerization reagent pool set is designed for isolating nucleic acid molecules having a nucleotide sequence different from a reference sequence in a locus of interest according to the methods described herein (e.g., as summarized above).

In certain embodiments, the two dideoxyribonucleotides are labeled.

In certain embodiments, the label is a member of a binding pair.

In certain embodiments, the label is a detectable label.

In certain embodiments, the polymerization reagent pool set has from about 12 to about 100 polymerization reagent pools.

BRIEF DESCRIPTION OF THE DRAWINGS

The invention is best understood from the following detailed description when read in conjunction with the accompanying drawings. It is emphasized that, according to common practice, the various features of the drawings are not to-scale. Indeed, the dimensions of the various features are arbitrarily expanded or reduced for clarity. Included in the drawings are the following figures:

FIG. 3 shows one embodiment of the sequence variant isolation method of the present invention for non-symmetric reference sequences.

FIGS. 4A and 4B show one embodiment of the sequence variant isolation method of the present invention for symmetric reference sequences.

FIGS. 5A, 5B, 5C and 5D show one embodiment of the sequence variant isolation method of the present invention for di-nucleotide repeat reference sequences.

FIGS. 6A and 6B show embodiments of the sequence variant isolation method of the present invention for reference sequences having a nucleotide repeat sequence.

FIGS. 7A and 7B show an embodiment of the sequence variant isolation method of the present invention for detecting changes in the number of bases in a nucleotide repeat sequence in a reference sequence using a specifically designed polymerization primer.

DEFINITIONS

Figure 1:
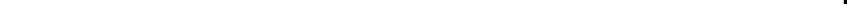
FIGS. 1A, 1B and 1C show steps in a method of making nucleic acid duplexes asymmetric.
Figure 1:
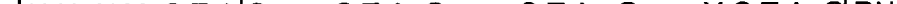

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e., a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, LNA's and the like, that may be employed. A "mismatch" in a duplex between two oligonucleotides or polynucleotides means that a pair of nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "Reference Sequence" below).

"Genetic variant", "variant", "variant nucleic acid" and equivalents means a substitution, inversion, insertion, or deletion of one or more nucleotides at a genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population (e.g., polymorphisms, mutations, etc). (See description below of Reference Sequence and Nucleic Acid. The terms "variant nucleic acids" and "non-variant nucleic acids" are also used with respect to the Reference Sequence.)

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 mL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TaqMan®"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" is used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, LNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g., including modified bases, sugars, or internucleosidic linkages. It is clear to those skilled in the art that where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (as measured in ° C.) at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3'direction, i.e., the direction in which a nucleotide polymerase polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

"Reference sequence" is used herein to denote a sequence to which a locus of interest in a nucleic acid is being compared. In certain embodiments, a reference sequence is considered a "wild type" sequence for a locus of interest. A nucleic acid that contains a locus of interest having a sequence that varies from a reference sequence for the locus of interest is sometimes referred to as "polymorphic" or "mutant" or "variant nucleic acid." A nucleic acid that contains a locus of interest having a sequence that does not vary from a reference sequence for the locus of interest is sometimes referred to as "non-polymorphic" or "wild type" or "non-variant nucleic acid". In certain embodiments, a locus of interest may have more than one distinct reference sequence associated with it (e.g., where a locus of interest is known to have a polymorphism that is to be considered a normal or wild type).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The invention is drawn to isolating nucleic acids having a sequence within a locus of interest that is different from a reference sequence for the locus of interest (e.g., isolation of a nucleic acid having a mutation or polymorphism in a locus of interest). In certain aspects, a mixture of nucleic acids, each having a locus of interest, are subjected to an iterative primer extension method targeted within the locus of interest (e.g., using a polymerization primer that hybridizes immediately upstream or within the locus of interest). The primer extension reactions are rationally designed based on the reference sequence for the locus of interest such that variant nucleic acids incorporate at least one distinguishing nucleotide into the polymerizing strand as compared to non-variant (or wild type) nucleic acids. Incorporation of this at least one distinguishing nucleotide allows the subsequent isolation of any variant nucleic acid strand(s) from non-variant strands. In other words, the iterative primer extension reactions are configured to allow the isolation of variant nucleic acid strands from non-variant strands at a locus of interest by virtue of the identity of the specific nucleotide(s) incorporated (or not incorporated) during the primer extension (or nucleotide synthesis) reactions.

For example, iterative polymerization reactions can be configured such that nucleotide polymerization from the polymerization primer through a locus of interest will continue if the sequence of the nucleic acid being analyzed matches the reference sequence for the locus of interest, whereas polymerization will be terminated, by incorporation of a dideoxynucleotide, if the sequence of the nucleic acid being analyzed does not match the reference sequence. The terminated strand can then be isolated from non-terminated strands using one of a number of methods (discussed in detail below). Nucleic acid strands that have mutations (or variations) can be isolated from wild type (or non-variant) strands in the sample using a variety of methods.

In certain embodiments, performing the iterative polymerization reactions on both strands (Watson and Crick strands) of the nucleic acids being analyzed through the locus of interest in separate reactions allows detection of nucleic acids having virtually any type of mutation.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the present invention provides methods and compositions for isolating one or more nucleic acids that have a sequence variation as compared to a reference sequence for a locus if interest. Aspects of the invention employ an iterative base-by-base nucleic acid polymerization process to analyze the nucleic acid molecules in a nucleic acid sample (e.g., a sample containing a mixture of nucleic acids from different subjects) through a locus of interest for which a reference sequence is known. To initiate this iterative base-by-base nucleic acid polymerization process, a polymerization primer is annealed immediately upstream of the locus of interest in the nucleic acids in the sample. The nucleotide sequences downstream of the annealed primer (i.e., in the locus of interest) are then analyzed (or interrogated) by performing iterative, template-based nucleotide extension reactions that are configured such that nucleic acids having a sequence different from the reference sequence (i.e., variant nucleic acids) can be isolated from nucleic acids having a sequence identical to the reference sequence (i.e., non-variant nucleic acids).

Nucleic Acids

Nucleic acids in a nucleic acid sample being analyzed (or processed) in accordance with the present invention can be from any nucleic acid source provided that the nucleic acids contain a locus of interest for which at least one reference sequence is known. In certain embodiments, a locus of interest will have more than one reference sequence associated with it (described in more detail below). As such, nucleic acids in a nucleic acid sample can be from virtually any nucleic acid source, including but not limited to genomic DNA, complementary DNA (cDNA), RNA (e.g., messenger RNA, ribosomal RNA, short interfering RNA, microRNA, etc.), plasmid DNA, mitochondrial DNA, etc. Furthermore, as any organism can be used as a source of nucleic acids to be processed in accordance with the present invention, no limitation in that regard is intended. Exemplary organisms include, but are not limited to, plants, animals (e.g., reptiles, mammals, insects, worms, fish, etc.), bacteria, fungi (e.g., yeast), viruses, etc. In certain embodiments, the nucleic acids in the nucleic acid sample are derived from a mammal, where in certain embodiments the mammal is a human.

In certain embodiments, the nucleic acids in the nucleic acid sample are enriched prior to analysis. By enriched is meant that the nucleic acid is subjected to a process that reduces the complexity of the nucleic acids, generally by increasing the relative concentration of the locus of interest. For example, nucleic acids in a starting nucleic acid sample can be digested with a specific restriction enzyme (or enzymes) such that the locus of interest is contained within a restriction fragment of a known size. Selection of nucleic acid fragments from this digested sample that encompass this known size (or removal of fragments different from this known size) will produce a nucleic acid sample that is enriched for the locus of interest. There are a wide variety of ways to enrich nucleic acids having a specific characteristic or sequence (e.g., a locus of interest), and as such any convenient method to accomplish this may be employed.

In certain embodiments, enrichment can be done by using an oligonucleotide probe that is complementary to a sequence present on a nucleic acid having the locus of interest (e.g., within the locus of interest). For example, if the locus of interest is known to be present in a particular gene, such as the p53 gene, an oligonucleotide probe can be used that is complementary to a sequence found in the gene of interest to facilitate enrichment of nucleic acids containing the locus of interest by hybridization. In certain embodiments, an oligonucleotide probe that is complementary to a nucleic acid fragment of interest can be constructed to include a first member of a binding pair to facilitate separation of the nucleic acid fragments of interest. Exemplary binding pairs include, but are not limited to, biotin and avidin, biotin and streptavidin, and the like. Other binding elements that can also be used to separate fragments of interest include magnetic beads, such as DYNABEADS™. In such embodiments, the oligonucleotide probes are immobilized to the first binding member of the binding pair, such as biotin, avidin, streptavidin, or a magnetic bead, and the probes are then incubated with the starting sample of nucleic acids under condition that allow hybridization between the oligonucleotide probes and the nucleic acid fragments if interest (e.g., rendered single stranded). Following an adequate amount of time, the hybridized probes as well as the tagged fragments of interest can be separated from the remaining population of tagged nucleic acids using the second member of the binding pair, such as avidin or streptavidin if biotin is used, or a magnet if a magnetic bead is used. This process can be used to select for a specific strand of the nucleic acids in the nucleic acid sample for analysis, where in certain embodiments both strands of a nucleic acid containing the locus of interest are selected sequentially and analyzed independently.

In certain embodiments, nucleic acids in the nucleic acid sample are amplified prior to analysis. In certain of these embodiments, the amplification reaction also serves to enrich a starting nucleic acid sample for the locus of interest. For example, a starting nucleic acid sample can be subjected to a polymerase chain reaction (PCR) that amplifies a region that includes the locus of interest. In certain embodiments, the amplification reaction is an exponential amplification reaction whereas in certain other embodiments, the amplification reaction is a linear amplification reaction. Any convenient method for performing amplification reactions on a starting nucleic acid sample can be used in practicing the subject invention. In certain embodiments, the nucleic acid polymerase employed in the amplification reaction is a polymerase that has proofreading capability (e.g., phi29 DNA Polymerase, *Thermococcus litoralis* DNA polymerase, *Pyrococcus furiosus* DNA polymerase, etc.).

In certain embodiments, the nucleic acid sample being analyzed is derived from a single source (e.g., a single organism, tissue, cell, subject, etc.), whereas in other embodiments, the nucleic acid sample is a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. As described above, the nucleic acids in nucleic acid samples from a single source as well as from multiple sources include a locus of interest for which at least one reference sequence is known.

In embodiments where a pooled nucleic acid sample is processed, the nucleic acids derived from each of the sources may be uniquely tagged such that after isolation of the variants according to the present invention, the source from which the variant nucleic acid was derived can be determined. Any convenient method for uniquely tagging nucleic acids from multiple sources may be employed, including but not limited to those described in co-pending U.S. patent application Ser. No. 11/656,746, filed on Jan. 22, 2007, and titled "Nucleic Acid Analysis Using Sequence Tokens", which is incorporated herein by reference in its entirety for its description of nucleic acid tagging and decoding.

A brief description of exemplary sequence tokens according to U.S. patent application Ser. No. 11/656,746 is provided here for clarity and is not intended to limit the scope of the present invention with regard to uniquely tagging nucleic acids. The exemplary tagging system is based on a 4-fold dimensionality with an 8 sequence token base at each level to facilitate tagging nucleic acids from up to 4,096 individual starting sources (8×8×8×8=4096). In this system, a first set of 8 unique sequence tokens are used in the first position "P" (e.g., sequence tokens 25 to 32), a second set of 8 unique sequence tokens are used in the second position "Q" (e.g., sequence tokens 17 to 24), a third set of 8 unique sequence tokens are used in the third position "R" (e.g., sequence tokens 9 to 16), and a fourth set of 8 unique sequence tokens are used in the fourth position "S" (e.g., sequence tokens 1 to 8). Therefore, this exemplary system requires a total of 32 individual sequence tokens (8+8+8+8=32) to uniquely label nucleic acids from up to 4,096 distinct sources. It is noted here that the position of the P, Q, R and S sequence tokens is generally dependent on the specifics of the assay in which they will be used. As such, no restriction in this regard is intended.

In order to achieve the tagging of each nucleic acid sample in a starting set of 4,096 nucleic acid samples, the 4,096 starting nucleic acid samples are first tagged in the "P" position with one sequence token from the set of 8 sequence tokens numbered 25 through 32 in repeating sequential order. For example, nucleic acid samples 1 to 8 are tagged with P25 to P32, respectively, samples 9 to 18 are tagged with P25 to P32, respectively, etc., until all samples are tagged with a P sequence token. Once completed, each respective P25 to P32 set of nucleic acid samples are pooled, producing 512 P-tagged samples. For example, P-tagged samples 1 to 8 are pooled to make P-tagged pool 1, P-tagged samples 9 to 18 are pooled to make P-tagged pool 2, etc., until all P-tagged samples are pooled. Next, the 512 P-tagged pools, each containing 8 original nucleic acid samples, are tagged in the second "Q" position with the second set of 8 sequence tokens (numbered 17 through 24) in repeating sequential order from 17 to 24. For example, P-tagged pools 1 to 8 are tagged with Q17 to Q24, respectively, P-tagged pools 9 to 18 are tagged with Q17 to Q24, respectively, etc., until all P-tagged pools are tagged with a Q sequence token. Once completed, each respective Q17 to Q24 set of nucleic acid samples are pooled, producing 64 PQ-tagged pools. For example, P-tagged pools 1 to 8 are pooled to make PQ-tagged pool 1, P-tagged pools 9 to 18 are pooled to make PQ-tagged pool 2, etc., until all P-tagged pools are pooled into a PQ-tagged pool. Next, the 64 PQ-tagged pools, each a pool of 64 original nucleic acid samples, are tagged in the third "R" position with the third set of 8 sequence tokens (numbered 9 through 16) in repeating sequential order from 9 to 16. Again, once completed, each respective R9 to R16 set of nucleic acid samples are pooled, producing 8 PQR-tagged pools (e.g., PQ-tagged pools 1 to 8 are pooled to make PQR-tagged pool 1, PQ-tagged pools 9 to 18 are pooled to make PQR-tagged pool 2, etc.). Next, the 8 PQR-tagged pools, each a pool of 512 original nucleic acid samples, are tagged in the fourth "S" position with the fourth set of 8 sequence tokens (numbered 1 through 8) in repeating sequential order from 1 to 8. All of the PQRS-tagged samples are then pooled to produce one sample containing all 4,096 starting nucleic acid samples, each of which contains a distinct PQRS-tag.

As a result of the unique sequence token tagging system, the correct sample identification of any tagged nucleic acid fragment isolated from the pooled population (e.g., a variant nucleic acid) can be readily determined based on the sequence tokens at each of the S, R, Q, and P positions (see U.S. patent application Ser. No. 11/656,746 noted above).

In certain embodiments, the nucleic acids in the nucleic acid sample being analyzed are immobilized on a substrate (e.g., a solid surface) during the iterative base-by-base polymerization process. The nucleic acids may be immobilized directly to the substrate via covalent linkage or via non-covalent interaction with an affinity ligand on the solid substrate. Exemplary affinity ligands include oligonucleotide probes that hybridize specifically to the nucleic acids being analyzed, e.g., an oligonucleotide that is complementary to a nucleic acid sequence within (or on the same nucleic acid fragment as) the locus of interest. In certain of these embodiments, the immobilizing oligonucleotide is the polymerization primer of the polymerization reaction. The substrate can be any of a variety of substrates known in the art for nucleic acid immobilization (e.g., magnetic particle, Sepharose™, agarose, silicone, nitrocellulose, etc.) so long as it does not interfere with the nucleic acid polymerization reactions of the assay. The substrate may take any convenient form, including but not limited to beads, pins, membranes, columns, etc.

In certain embodiments, the nucleic acids assayed are rendered single stranded prior to analysis. In certain of these embodiments, each strand of a duplex nucleic acid are processed independently through the region of interest. As will be described in further detail below, in certain embodiments, depending on the specifics of the reference sequence and the variation in question, processing of both strands of a variant nucleic acid may increase the effectiveness of isolating it according to the present invention.

In certain embodiments, the single-stranded nucleic acid sample being processed is enriched for a specific strand of a double-stranded starting material. Enriching for a specific strand can enhance the efficiency and effectiveness of processing by reducing background cross-hybridization reactions that may occur between the strand of the nucleic acid serving as the template in the polymerization reaction and its complement. Rendering nucleic acids single-stranded may be done using any convenient method, which may include, but is not limited to, amplifying the nucleic acid strand of interest using an asymmetric PCR or linear amplification reaction, strand specific immobilization, etc. For example, a nucleic acid sample can be rendered into two, complementary single-stranded samples by immobilizing each strand to independent substrates by hybridizing to immobilized oligonucleotides that target different strands of the nucleic acid, i.e., the oligonucleotides are complementary to different strands of the duplex.

In certain embodiments, double-stranded nucleic acids of the sample being analyzed are rendered asymmetric to facilitate the isolation and/or amplification of a single-stranded template for processing. Any convenient method for rendering a double-stranded nucleic acid asymmetric may be used.

For example, nucleic acids can be rendered asymmetric using the following process. As will be seen in the description below (and FIG. 1) this method of making nucleic acid duplexes asymmetric does not require the incorporation of a modified base and thus avoids the difficulties associated with such a requirement. This process enables the easy production of single-stranded copies which are immobilized and/or utilized in the typical implementation of the present invention.

The enzyme dam methylase, which is commercially available, converts the nucleotide A to 6-amino methyl A when present in the restriction sequence GATC of a nucleic acid. The common enzyme BstYI cuts the site RAGATCY (where R is a purine and Y is a pyrimidine) regardless of its methylation status at A. Therefore, BstYI cuts non-, half- and fully dam methylated sites. In contrast, the enzyme DpnII cuts AGATC only in its non-dam methylated form (i.e., this site is protected by both half and full dam methylation).

To generate asymmetric DNA, the starting double stranded DNA is first methylated at all GATC sites with dam methylase. It is then cut with BstYI generating fragments with all internal GATC uncut sites fully methylated and the single stranded ends cut with BstYI carrying a methyl A (see FIG. 1A).

After a single nucleotide fill in reaction (adds a single deoxy G nucleotide to prevent self ligation), we now ligate in an adaptor which tags both ends symmetrically (see box designated "adaptor" on in FIG. 1B). It is also possible to ligate an adaptor with an overhang that is complementary to the ends of the BstYI cut DNA (not shown in FIG. 1B). As used describing FIG. 1, an "adaptor" can be defined as a short duplex of substantially complementary oligonucleotides which are appended to another double stranded DNA sequence, usually by ligation. Ligating adaptors to the ends of nucleic acids is well known in the art. In general, adaptors (which in FIG. 1 is represented by the "N $N_x$ N", where x is an integer of about 10 or more), contain known sequences that can be exploited for a variety of uses (e.g., for use as a site for primer hybridization, e.g., for nucleic acid amplification). As shown in FIG. 1B, the A nucleotide that was added by the fill-in reaction (or that was part of the overhang of the adaptor) is not methylated. Thus, we have hemi-methylated GATC sites at both ends (see FIG. 1B).

We now denature the DNA and prime with biotin labeled primer that hybridizes to the adaptor, copying exactly once (using a DNA polymerase and dNTPs) generating the DNA shown in FIG. 1C. All of the internal GATC sites are now half methylated while the extended site on one end is half methylated while the other is unmethylated. We now cut with DpnII and only the arm on the left will be cut (i.e., the unmethylated site). We can use the biotin label to remove the end and any uncut material and we can now add via ligation a new adaptor (with appropriate tags, cut sites, primer sites, etc. as needed) to the cut end. Such a system allows for isolation of the same nucleic acid strand of a particular locus from a population of nucleic acids.

We have shown in FIG. 1C that the adaptor contains an R/Y pair adjacent to the GATC; this restores the BstYI site.

The method described above is but one exemplary method that can be used to create asymmetric DNA of one strand to use as the starting material for sequence variant analysis as described herein. Other methods known in the art may be used to produce asymmetric DNA, e.g., asymmetric PCR.

The locus of interest being analyzed using the process of the present invention can be any size, ranging from a single base to many kilobases in length (where, as described above, the locus of interest is contained within a nucleic acid molecule in the nucleic acid sample). For example, the assay may be employed to isolate a sequence variant at a single nucleotide position. In this example, the process may be carried out by analyzing both strands in independent reactions using polymerization primers that hybridize immediately upstream of the nucleotide of interest (in both directions). In this case, only two reactions need be carried out using as few as two polymerization reagent pools in total (described in detail below), one for each strand being analyzed (excluding wash and final extension pools, if employed). As another example, a locus of interest of as long as many kilobases in length (about 1 kilobase or more, about 2 kilobases or more, about 5 kilobases or more, up to and including about to about 10 kilobases or more) may be analyzed by employing multiple polymerization primers for each strand placed at desired locations along the locus of interest in separate reactions. In these embodiments, polymerization reagent pool sets having tens or up to a hundred or more polymerization reagent pools may be employed. In certain of these embodiments, the polymerization primers can be spaced at regular or irregular intervals, where by spacing is meant the distance between the 3' most base of one primer to the 3' most base of the next polymerization primer (in essence measuring the distance between the starting sites for polymerization). Because each polymerization primer is analyzed in a separate reaction, the primers may "overlap" one another. For example, a set of regularly spaced polymerization primers for a locus of interest may each be 30 nucleotides in length with a 15 base spacing. This means that consecutive primers will have a 15 base overlap. The number and spacing of polymerization primers will depend in part on the size of the locus of interest, the number of reactions to be processed in a single run, and the number of bases to be analyzed per polymerization primer.

Figure 2:
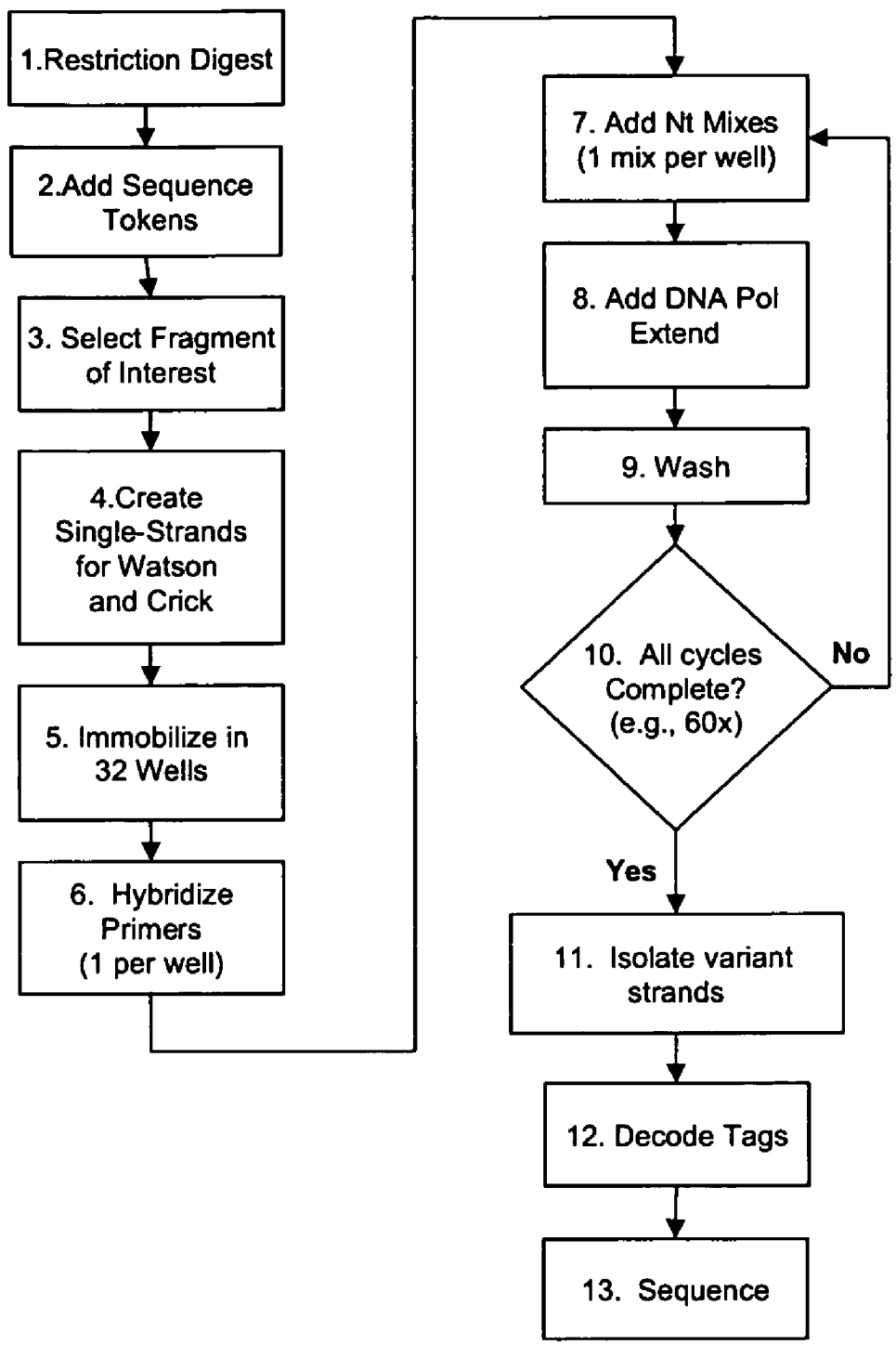
FIG. 2 provides an exemplary flow chart depicting one embodiment of the sequence variant isolation methods of the present invention.

FIG. 2 provides an exemplary outline of one embodiment of a nucleic acid variant analysis of the present invention. Details of some of the steps shown in FIG. 2 will be described in greater detail in subsequent sections.

As noted previously, the size of a locus of interest to be analyzed can vary widely, and include anywhere from a single base to up to many kilobases in length. Further, the number of bases that can be analyzed from a single polymerization primer can range anywhere from 1 to up to hundreds of bases. However, for the sake of the exemplary flowchart in FIG. 2, we will assume that the locus of interest is 960 bases in length and that 60 bases can be analyzed from a single primer, which translates to employing 16 primers per strand (i.e., a 960 base locus of interest/60 bases interrogated per primer=16 primers). Therefore, to cover analyzing both strands of the 960 base locus of interest, we will employ a total of 32 primers in 32 separate wells (i.e., 16 primers for the Watson strand and 16 primers for the Crick strand). Thus, in FIG. 2, 32 separate polymerization reactions in each round of the process will be performed (one reaction per well).

Steps 1 to 3 of FIG. 2 are drawn to the tagging and isolation of the nucleic acid sample that is to be analyzed. For example, nucleic acids from 1000 individuals can be assayed in a single run, each of which is uniquely tagged such that at the end of the assay, the original source of an isolated variant strand can be determined (e.g., by sequencing and or sorting). In steps 4 to 10, the nucleic acid sample is processed in an iterative fashion such that every nucleotide position is scored for whether it is the same as or a variant of a reference sequence. In step 4, the sample is rendered single stranded, with the Watson (W) and Crick (C) strands separated from one another (in certain embodiments, it is not necessary to separate the Watson and Crick strands prior to analysis as long as the polymerization primer can hybridize to its target site). In step 5, the nucleic acid sample is split into 32 aliquots, one for each polymerization reaction, and is immobilized (as noted below, this can be on the sides of wells, on beads, on pins, etc.); in step 6, a single polymerization primer is hybridized to the nucleic acids in each of the separately immobilized aliquots, providing a primer for nucleotide synthesis. In Steps 7 and 8, polymerization reagent pools are added to the wells according to the reference sequence that is immediately downstream of the polymerization primer (described in detail below). In steps 9 and 10, the polymerization reagent pool is washed away from the immobilized nucleic acid strands and a decision is made as to whether another polymerization step should be started or if the number of steps to be performed has been reached (in this case, the number of steps is assumed, for the purposes of this example, to be 60). In Steps 11 to 13, the variant strands are isolated, the sequence tags decoded, and the variation confirmed by sequencing (e.g., from the original sample from which the variant was derived).

It is noted here that FIG. 2 provides but one example of the workflow for isolating variant strands according to the subject invention. In certain other embodiments, one or more of the steps may be excluded, performed in a different order, or be configured in an alternative fashion. For example, the workflow shown in FIG. 2 may be reorganized such that after each extension reaction (step 8), variant strands are isolated (step 11) prior to adding the subsequent nucleotide mixes (step 7). Further, certain embodiments of the subject invention may include an amplification step in the workflow and/or using a number of different synthesis primers in successive steps of polymerization (e.g., after a specific number of rounds of polymerization). Certain variations to the workflow in FIG. 2 are described in further detail below.

The variant isolation processes described herein can detect variants in a locus of interest in a mixed nucleic acid sample (meaning a nucleic acid sample from multiple distinct individuals) that occur at a frequency of about 5% or less in the population being assayed, including at about 3% or less, 1% or less and even at a frequency of about 0.5% or less of the population being analyzed.

Polymerization Reagent Pools

As summarized above, the present invention uses an iterative base-by-base polymerization process to isolate nuclei acids having a sequence variation in a locus of interest as compared to a reference sequence. To accomplish this, the nucleic acids being processed are contacted to a series of defined polymerization reagent pools comprising a defined set of polymerization reagents. Together, the defined polymerization regent pools employed in processing a nucleic acid sample are called a polymerization regent pool set. In certain embodiments, each of the polymerization reagent pools in a polymerization reagent pool set comprises a nucleotide polymerase (e.g., a DNA polymerase, e.g., T7 DNA polymerase or the like) and at least one nucleotide base (e.g., one or more deoxyribonucleotide [dNTP], one or more dideoxyribonucleotide [ddNTP], or any combination thereof), where the selection of the nucleotide base in each of the polymerization reagent pools is based on a reference sequence for a locus of interest. In certain embodiments, one or more polymerization reagent pool in a polymerization reagent pool set comprises at least one dNTP and at least one ddNTP. In certain embodiments, the ddNTP(s) in a polymerization reagent pool is labeled with either one or both of a binding moiety and a detectable label, wherein in certain embodiments, a single moiety can serve as both a binding moiety and a detectable label. For example, a fluorescent tag can be used as an identifying label and a binding moiety, with its binding partner being an antibody to the fluorescent tag. In certain embodiments, polymerization reagent pool sets include polymerization reagent pools having ribonucleotides, multiple deoxyribonucleotides, or additional enzymes (e.g., other than or in addition to the nucleotide polymerase).

In certain embodiments, a polymerization reagent pool set comprises one or more wash pools or reservoirs, where the wash pools or reservoirs are employed to wash the nucleic acids in between contacting to each polymerization reagent pool.

In certain embodiments, a polymerization reagent pool set has from about 10 to about 100 polymerization reagent pools. In certain embodiments, each polymerization reagent pool in a polymerization reagent pool set comprises a distinct combination of polymerization reagents, whereas in other embodiments the polymerization reagent pool set comprises a certain number of duplicate polymerization reagent pools.

In certain embodiments, 12 polymerization reagent pools, each containing one dNTP, one absent nucleotide base and the remaining two nucleotides as ddNTPs (e.g., biotinylated ddNTPs) are used in the methods of the invention. In certain embodiments, one or more known mutation or polymorphism is to be ignored for a locus of interest (i.e., when there is more than one reference sequence for the locus or interest: e.g., a first "wild type" reference sequence and a second "polymorphic" reference sequence that includes the polymorphism to be ignored). In these embodiments, a polymerization reagent pool set will include one or more polymerization reagent pools that include more than one dNTP and a single (or no) ddNTP. As will be clear from the description of aspects of the invention below, the number and composition of polymerization reagent pools in a polymerization reagent pool set will be determined primarily on the nature of the reference sequence (or sequences) for the locus of interest.

As indicated above, in certain embodiments, the nucleic acid molecules in the sample being analyzed are immobilized to a surface, which allows: 1) their movement from one polymerization reagent pool to the next, (with washing steps in between); and/or 2) various solutions to be flowed past (e.g., wash and polymerization reagent solutions). As such, in certain embodiments, a polymerization reagent pool set is a composition comprising a series of fluids flowed past an immobilized nucleic acid (possibly with some incubation steps) rather than a set of distinct reagent pools into which the immobilized nucleic acid is contacted (e.g., dipped).

Polymerization/Termination Reactions

In describing the polymerization/termination reactions of the present invention, we will assume the following: First, we are analyzing a locus of interest in a nucleic acid sample using a single polymerization primer that is immediately upstream of a defined region of the reference sequence. As noted above, the invention can be carried out using multiple polymerization primers in distinct polymerization reactions based on the identity of the reference sequence immediately downstream of the polymerization primer. Second, the nucleic acids are immobilized on a surface that can be transported from polymerization reagent pool to polymerization reagent pool as indicated. Transport from reagent to reagent (with washings in between) can be done manually, but will preferably be implemented using computer-assisted control and robotics.

We will use the following conventions in the description below (in text and/or Figures):

A, G, C and T are deoxyribonucleotides;

> is used to denote di-deoxynucleotide terminators (and thus mutations/variations scored);

N! (e.g., A!, G!, C!, or T!) represents a vacancy in the polymerized strand that could be, but is not, currently filled (N! is not used after a terminator has been added to a polymerizing strand because no nucleotide can be added).

W (Watson) and C (Crick) refers to the two complementary strands the symbol "~"=complement of a nucleotide "muts"=mutations that can be identified at each location employing the synthesis algorithm described above As discussed in detail below, in certain embodiments, the di-deoxynucleotide terminators employed in the present invention may labeled with a first member of a binding pair (e.g., a biotin moiety) to facilitate variant strand retrieval once the polymerization steps have been completed (e.g., using an avidinylated substrate). In certain other embodiments, variant strand retrieval is achieved without the need for a binding moiety, and thus the terminators are not labeled. In addition, the polymerization reactions described below assume that an appropriately designed and hybridized polymerization primer is employed, the design of which is well within the capabilities of those of ordinary skill in the art.

Non-Symmetric Reference Sequences

Consider first a simple sequence where there are no homopolymer stretches of a particular base and no symmetric triplets, e.g., XYX: In such a simple sequence the 5' and 3' neighbors of any base in the reference sequence are different from each other and from the base itself.

For example, consider the reference sequence: 5'-ACT-AGCT-3' (see FIG. 3, W strand), which corresponds to the bases that should be added immediately downstream of the polymerization primer hybridized to the nucleic acid strand being analyzed. At each base position of this reference sequence, there are 3 potential variations (or mutations). In this example, the T in the template strand (the Crick or 'C' strand in FIG. 3) could be changed to any one of A, C or G, which would change the next base added upon polymerization from the expected A to T, G or C, respectively. Because by definition the reference sequence (or sequences) is known beforehand, we know that the next base that should be added after the first A is C (i.e., the base added at position 2 will be a C if it is the same as the reference sequence). Therefore, the first polymerization reagent pool employed includes the following mix of nucleotides: A (the "correct" base), G> and T> (two potential "mutant" bases), but not C>. The reason C> is not used in the first polymerization reagent pool is because it would terminate a non-variant sequence at the base immediately following the correct base (i.e., the C at position 2 after the A at position 1) after incorporation of the correct base (i.e., A), thereby erroneously terminating polymerization and labeling a non-variant sequence as a variant.

As such, at position 1 of the reference sequence, synthesis will be terminated if the sequence variation is a G or a T while the sequence will halt if the variation is a C (i.e., this position will be left vacant). Note that in a situation where a sequence varies from the reference sequence above by changing the first A to a C, the vacant position will be filled in when we move to the next base because the reference sequence has a C at the second position (and thus C will be included in the polymerization reagent pool). In this simple example, an A to a C variation at position 1 (meaning that the base in the complementary strand is a G rather than a T) will not lead to strand termination. However, as described below, such a variation can be recovered in later steps of the process or in processing of the complementary strand.

After completion of the first polymerization reaction, the polymerization reagents of the first polymerization reagent pool are washed away in preparation for contacting to the next polymerization pool. As noted above, in certain embodiments, the template nucleic acid strands in the nucleic acid sample being processed are immobilized on a solid support (or station), e.g., a pin or bead or well. In these embodiments, the polymerization reagents may be washed away by flowing a wash solution over the support and/or transferring the substrate to a wash pool present in the polymerization reagent pool set. In embodiments in which the nucleic acids being analyzed are not immobilized, the polymerization reagents can be removed by other convenient methods, including but not limited to precipitation, filtering, by size exclusion separation, destruction of active reagents (e.g., heat inactivation, enzymatic destruction), etc.

After washing, the process of contacting the nucleic acids to the next polymerization reagent pool, incubating, and washing, continues in a stepwise (or iterative) process through the sequence applying at each step n the reference sequence base at the site n and, of the three potential variants, terminators omitting the one corresponding to (n+1) base. Formally, this corresponds to using $X_n+[N>-(X_n>+X_{n+1}>)]$, where $X_n$ is the reference sequence nucleotide to be added at the current position, $X_{n+1}$ is the nucleotide to be added at the next position in the reference sequence, and N> is all dideoxynucleotides.

Employing this algorithm will at a minimum allow termination (and thus isolation) of a variant sequence having 2 of the three mutations at any given position.

As noted above, however, there are situations in which a variant may elude chain termination (e.g., as noted above for an A to C variation in the reference sequence in FIG. 3). To obtain the third potential variation, we now apply the same procedure to the complementary strand derived from the same region of interest of the nucleic acid being analyzed. For the sequence above, the complementary sequence is as follows: 5'-AGCTAGT-3' (FIG. 3). In this case, the (n+1) base corresponds to the (n−1) base on the complementary strand. Because by definition these are different base pairs, we lose a different mutation as shown in FIG. 3. By analyzing both strands of the nucleic acid, mutations missed in the analysis of one strand are detected in the analysis of the other strand.

In FIG. 3A, the W strand is processed from the top to the bottom while the C strand is processed from the bottom to the top (as indicated by the arrows). When the totality of the mutations that can be identified for each position of the reference sequence after processing both the W and C strands, i.e., by adding the W "muts" column with the ~C "muts" column, it is seen that all three possible mutations at each site can be identified for this class of sequence [see the (W+~C) "muts" column in FIG. 3].

As noted above, in certain embodiments, more than one reference sequence is used in processing a nucleic acid sample according to the subject invention. By more than one reference sequence is meant that one or more specific base locations in the locus of interest being analyzed has a known variant that is to be ignored. In these embodiments, the polymerization reagent pool set will include polymerization reagent pools that include more than one dNTP (i.e., a dNTP for each known base at that position). Therefore, we can deal with known variations in a locus of interest with special polymerization reagent pools where all known nucleotide variants are present at the requisite step (i.e., use of special regent pools in which multiple deoxyribonucleotides are present which represent variants that are to be ignored in the analysis).

Symmetric and Repeat Sequences

We have shown above that all possible mutations can be retrieved from simple sequences with asymmetrical triples provided that we carry out the scanning of both chains of DNA. At first sight, it appears that this would not be achieved with symmetrical triples, because XYX, the (n−1) and (n+1) base pairs surrounding the central base Y are identical. However, owing to a particular feature of the scanning method, this is not so, as can be seen from the following example.

Consider the triplet GTG in the sequence AGTGC, where the possible mutant sequences of the T base in the GTG triplet are: GCG, GAG and GGG (FIG. 4; the wild type and mutant reference sequences are denoted from top to bottom in a 5' to 3' direction, similar to the W strand in FIG. 3). We first scan A by adding A, C> and T> which results in an A added at the first position (see "polymerizing strand" column to the right of each sequence in FIG. 4A).

We next scan for G using G, A>, and C>, which is shown in FIG. 4B. Note that the reference sequence is held up, by design, at a vacancy (T!) because neither T or T>was included in the polymerization reagent pool, but the three mutant sequences are captured: C and A mutations are captured by direct chain termination at the mutated base location whereas the G mutation leads to a run of G bases that is filled in with G and terminated at the C at position 5 of the reference sequence (i.e., incorporates C>), which is at a position other than at the mutated base. As such, termination in a variant/mutant strand can occur at the specific site of a variation/mutation or may occur at a position other than the variation/mutation depending on the nature of the reference sequence and the specific variation/mutation present in the nucleic acid.

We may now examine doublet repeat sequences (e.g., XYXYXY) in a reference sequence. We will first consider the sequence AGTGTGC and follow a T to G change in the first GTG triple (FIG. 5). As discussed above, the other two possible mutations at this site will be captured by incorporation of a terminator at the site of the mutation. We begin by scanning A with A, C> and T>, as shown in FIG. 5A. Next we scan the G with G, A> and C>, which, as shown in FIG. 5B, both stop at a T vacancy (T!). After scanning with a T, both move forward but the sequence is now one repeat ahead as shown in FIG. 5C. We now scan for G using G, A> and C>, as shown in FIG. 5D. As shown, the wild type (or reference) sequence is arrested at a T vacancy (T!) while the mutant has been terminated by incorporation of a C> at position 7. The chain has thus been terminated at a location that is downstream of the variant/mutant base in the nucleic acid. In this example, the variant/mutation was captured because it advanced the polymerizing strand one repeat ahead of where a wild type polymerizing strand would be, leading to strand termination when the variant strand had exited the repeat region (and the wild type had not).

We note that doublet repeat $(GT)_n$ may also be considered as $(TG)_n$ with triples TGT. Using the same algorithm above, we can show that G to T mutations can be recovered in such repeats. In the sequence shown in FIGS. 4 and 5, we will not be able to find A to G changes in the first base, but will be able to find the equivalent change in reverse scanning as we have already provided to be the case (see above). In the reverse sequence, the repeats are $(AC)_n$, generating triples ACA, or they can be treated as $(CA)_n$ with CAC triples. In both cases we recover all mutations both for C and A. In fact, except for first and last bases, such sequences need only be scanned in one direction.

As stated above, creating a triple of G or T essentially advances the mutant sequence by one repeat and thus will be true wherever the mutation generates this in a repeated sequence. This suggests that we can use this method to sort repeats which are either longer or shorter than some given number.

Consider the general case T $(CATG)_n$ A. Suppose we have scanned the first repeat CATG. The molecules with exactly 1 repeat will be considering the doublet GA, while those with more that one repeat are dealing with GC (the G being the last base of the repeat, the A representing base after the G in a single repeat, and the C representing the beginning of a second repeat). We can, therefore, by chain terminating with A> remove all the molecules at end of n cycles with n repeats and leave those to be continued. This allows us to count repeats accurately and to separate molecules with a given number of repeats. The methods find use in analyzing genome stability because it would essentially tag molecules that are shorter or longer than some given number, n.

We will now consider runs of bases, for example the run of Gs in the sequence TGGGGAC (FIG. 6). We enter the run using G, C> and T>. The wild type (reference) will incorporate G's to the end and stop at the A vacancy (A!). As such, any G to C and G to T changes in the repeat will be captured by termination (not shown). Any G to A changes will be held up at A vacancies (A!) FIG. 6A. When we scan for A with A, T> and G>, all of these A vacancies except the last will be filled and converted to G vacancies, which will be promptly terminated. Analyzing the complementary strand will capture the G to A change in the last base of the run of Gs (i.e., it will be a C to T change in the first base of a run of Cs).

Thus, any run of bases $X_n$ behaves as though it were a single base and we may write this in reduced form $\underline{X}$. Thus we can convert $A(G_n)T$ to $A\underline{G}T$ and treat it as though it was one base. In the Examples of dinucleotide repeats given above, the sequence change T to G at position 2 converts GTGT to GGGT. Rewriting the mutated sequence as $\underline{G}T$ reveals that the $(GT)_2$ has been converted to $(GT)_1$ with the loss of a repeat, which we have shown above will be captured. By the same token, in the sequence GGTGG we will recover all possible mutations of T, because we can rewrite it as $\underline{GT}\underline{G}$ and have proved above for GTG that this can be achieved. Basically, the change T to G gives a continuous run of Gs and this will be the case independent of the number of Gs before or after the T base.

Higher level repeats such as $(GGA)_n$ repeats can be dealt with in the same way. All mutations will be retrievable because this reduces to $(GA)_n$ or $(AG)_n$ doublet repeats.

Homopolymeric Sequences

The scanning method described above may have difficulty detecting changes in the number of bases in single base repeat sequences because it treats all runs of bases as a single nucleotide. However, we show here that by choice of the primer, additions can be detected and if the displacement method for strand elution is used (described in detail below), deletions will be detected as well.

Suppose we have a run of 4As followed by CGT and we wish to detect changes in the number of As. We construct a primer terminating in 4Ts so the first base to be sequenced in the reference sequence will be a C as shown in FIG. 7A. If we have an increase in the number of As, the first base in a mutant with any increase will be an A as shown in FIG. 7B for an increase of 1 base. This will be detected and terminated.

Note that if we have a reduction in the number of bases to 3As or less, the primer will not match at the 3' T base and thus will not support polymerization. Because we can capture any nucleic acid strand that cannot support nucleic acid polymerization (described in more detail below), the inability to initiate polymerization due to a non-complementary 3' base is equivalent to being terminated by incorporating a dideoxynucleotide, and these variants will be detected and selected as well.

The amount of time required for processing can vary widely, depending on the nature of the analysis, e.g. the number of cycles, the time for performing each cycle, etc. The time required for each cycle, which includes polymerization and washing, can range from about 1 minute to about 10 minutes, including from about 2 to 6 minutes and including from about 2 to 3 minutes. Going back to the example in FIG. 2, if we perform about 60 cycles and each step takes about 2 to 3 minutes for incorporation and washing, the entire process can be completed in about 2 to 3 hours. In the methods of the invention, the incorporation yield of deoxynucleotides in each round will be greater than about 95%, including up to about 98% and up to about 100%. The yield of incorporation of dideoxyribonucleotides may be lower, including from about 75% yield or more.

We have shown that provided we scan for both the direct and inverse complementary strands of a reference sequences, we can scan and extract all mutants (or variants) from all sequences. To do this we start with a reference sequence for the locus of interest, which guides the path of addition of polymerization reagent pools. If there are known variants at a given site (e.g., abundant polymorphisms which appear in a significant percentage of the population, perhaps greater than 20%, more often as much as 50%) so that we are scanning more than one sequences at a single position, we simply include dNTPs for the known variant(s) (while removing the ddNTP for that variant in the polymerization reagent pool at issue). Therefore, in certain embodiments, a polymerization reagent pool may include only one (or no) ddNTP. In certain embodiments, a polymerization reagent pool may include all four dNTPs and no ddNTPs.

As noted above, we can parallelize the scanning operation by using different primers to start at different points along both the sequences. In certain embodiments, from about 10 to about 200 rounds of synthesis are carried out in a single scanning run.

Eluting Nucleic Acids from a Substrate Using Strand Displacement Activity

Figure 8:
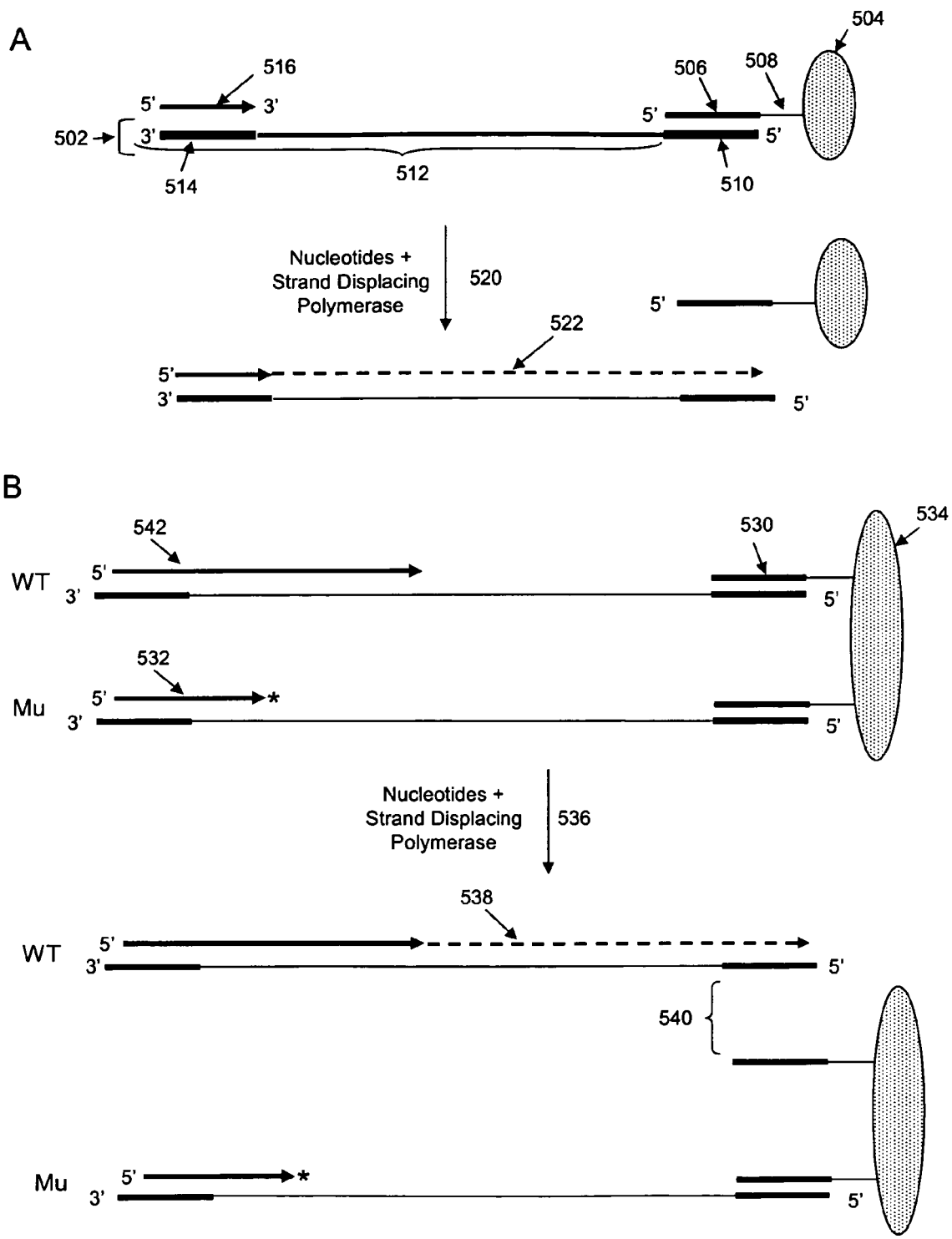
FIG. 8A illustrates certain aspects of using nucleotide synthesis by a strand-displacing polymerase to elute a nucleic acid from a capture primer attached to a substrate.
FIG. 8B illustrates an embodiment of employing strand displacement nucleotide synthesis to specifically elute non-variant nucleic acid strands from a capture primer attached to a substrate while leaving variant nucleic acid strands immobilized.

Certain nucleotide polymerases possess 5' to 3' strand-displacement activity (e.g., reverse transcriptase, Bst DNA polymerase, Bca DNA polymerase, phi 29 DNA polymerase, etc.). As shown in FIG. 8A, this activity can be exploited as a way to elute nucleic acids from an immobilization oligonucleotide (or capture primer) attached to a substrate (e.g., a bead, pin, well, etc.).

In FIG. 8A, capture primer (506) is attached to a substrate (504) through linker (508) with the 3' end proximal to the substrate. Nucleic acid (502) is immobilized to the substrate by hybridization to the capture primer through a region in the nucleic acid that is complementary (510) to the capture primer (also called the capture primer binding site). This capture primer binding site in the nucleic acid may be one that has been specifically added to the nucleic acid (e.g., a ligated adaptor or nucleic acid tag) or one that is normally present in the nucleic acid (e.g., a specific genomic region), and as such, no limitation in this regard is intended. As is depicted in FIG. 8A, the immobilized nucleic acid includes a region that is upstream of the capture primer binding site (512). This upstream region includes a polymerization primer binding site (514), with the arrow indicating the direction of polymerization from this primer (i.e., 5' to 3'). As with the capture primer binding site described above, the polymerization binding site in the nucleic acid may be one that has been specifically added to the nucleic acid (e.g., a ligated adaptor or nucleic acid tag) or one that is normally present in the nucleic acid (e.g., a genomic region), and as such, no limitation in his regard is intended.

To elute the nucleic acid from the capture primer (and thus the substrate), a polymerization primer (516) is hybridized to the nucleic acid at the polymerization primer binding site (514) and nucleic acid synthesis is initiated by adding nucleotides (e.g., all four dNTPs) and a strand displacing polymerase under nucleic acid polymerization conditions (step 520; dotted line 522 indicates nucleic acid synthesis). When the polymerase encounters the capture primer (506), its 5' to 3' displacement activity removes the capture primer from the nucleic acid, thereby eluting the nucleic acid from the substrate.

It is noted here that the capture primer and the polymerization primer need not hybridize to the extreme ends of the nucleic acid as depicted in FIG. 8A. Rather, it is the relative positions of the capture primer and the polymerization primer that are relevant to elution by strand displacement synthesis. Specifically, the polymerization primer must hybridize upstream of the capture primer on the nucleic acid being eluted.

Immobilization of nucleic acids and elution by strand displacement is particularly useful in processing mixtures of nucleic acids because it provides for multiple levels of control of the process. First, nucleic acids will be immobilized only if they contain a region that hybridizes to the capture primer (or primers) attached to the substrate. Second, only nucleic acids having the polymerization primer binding site will be capable of elution. And third, only polymerization primer-hybridized nucleic acids capable of supporting nucleotide synthesis all the way through the capture primer will be eluted. This third element is a product of the ability of the polymerization primer to support polymerization (e.g., has the polymerization strand been terminated by incorporation of a dideoxyribonucleotide) and on the composition of the nucleotides in the polymerization reaction (e.g., are the species of nucleotide bases in the polymerization reaction sufficient to complete polymerization on the nuclei acid template). These levels of control allow one to elute only nucleic acids of interest while leaving other nucleic acids immobilized on the substrate, a result that cannot be achieved using conventional techniques for primer/template denaturation (e.g., chemical or heat denaturation). Thus, strand displacement elution can be used in any variety of nucleic acid isolation or nucleic acid sorting processes (some of which are described below).

Variant Strand Isolation

Isolation Using Binding Moiety Interaction

As discussed above, in certain embodiments, the chain terminators employed in the process of the invention are labeled with a binding moiety (e.g., biotin). As such, strands in which polymerization has been terminated can be selected by binding to their cognate binding partner (e.g., avidin) and the tagged templates released by melting. These will contain the starting mutant strands, which can be cloned into vectors or produced as amplified PCR products and accurately sequenced by any convenient method (e.g., Sanger sequencing) (or sequenced directly, depending on the amount of starting material and the yield).

As such, in certain embodiments, at the end of iterative steps of the polymerization process, the template strands and hybridized polymerization products are detached from the solid surface and sorted by binding any labeled strands (e.g., strands containing biotinylated terminators) to the cognate binding partner for the binding moiety attached to the ddNTPs employed, as are known in the art (e.g., avidin/streptavidin). As described in detail above, these strands are the mutant/variation containing strands. The complete strand is released from the biotinylated partner by melting or appropriate enzyme degradation and all are converted to double strand form by priming and synthesis. These are the mutation containing sequences that were present in the original sample which can be sequenced or analyzed by any convenient method. In certain embodiments, the mutant strands isolated are cloned into vectors (e.g., sequencing vectors).

In embodiments in which the starting sample of nucleic acids are tagged (e.g., using sequence tokens), the tags of the collection of isolated nucleic acids may be sequenced to see how many and which individual samples are represented in the isolated variant population. From this information, one can isolate the original molecule from the original locus enrichment mixture from the properties of the tag (for example, by use of appropriate PCR primers or hybridization oligos) and sequence these to see whether the individual is homo or heterozygous for the identified variation (e.g. polymorphism).

Isolation Using Strand Displacement

As described above, in certain embodiments, the single stranded nucleic acids being analyzed are bound to an immobilized oligonucleotide complementary to a region present in the nucleic acid containing the locus of interest. As shown in FIG. 8B, the nucleic acids being processed are immobilized to substrate (534) via capture primer (530). Once we have carried out the process for the requisite number of rounds, wild type nucleic acids (WT in FIG. 8B; non-variant strands) are still polymerization-competent (i.e., from hybridized primer 542) while mutant strands (Mu in FIG. 8B; variant strands) are polymerization incompetent (e.g., due to the incorporation of a terminating dideoxynucleotide or due to non-complementarity at the 3' and of hybridized primer 532). The polymerization-incompetent site is indicated in FIG. 8B by an asterisk. It is to be understood that there may only one species of mutant immobilized on a substrate or multiple different species of mutant nucleic acids immobilized to the substrate, depending on the specific design of the variant analysis process.

These immobilized nucleic acids are contacted to a polymerization reagent pool that contains a polymerase having 5' to 3' strand-displacement activity and all nucleotides (e.g., a DNA polymerase and all 4 dNTPs) (536). On polymerization-competent complexes (i.e., non-variant, or wild type, nucleic acids), the strand-displacing DNA polymerase will complete synthesis (538) and displace the nucleic acid strand from the capture primer on the substrate (540). Conversely, in nucleic acids in polymerization-incompetent complexes (e.g., in which polymerization has been terminated; i.e., variant, or mutant, nucleic acids), no polymerization will occur and the nucleic acids will not be displaced from the immobilization oligonucleotide. As such, only nucleic acids having a sequence different from the reference sequence will remain immobilized on the substrate. These immobilized variant nucleic acid strands can be eluted by denaturation (e.g., by heating) after removal of the displaced, non-variant nucleic acids (e.g., by washing; the non-variant strands may be collected for additional processing if desired).

In certain embodiments, employing displacement elution of non-variant nucleic acid strands in this way may obviate the need to use binding moiety tagged ddNTPs in the polymerization reagent pools (e.g., biotinylated ddNTPs) for use in variant nucleic acid isolation (as described above). However, using binding moiety tagged ddNTPs will not interfere with using strand displacement elution of non-variant nucleic acid strands, and in certain embodiments both strand displacement and binding moiety tag isolation methods can be used (e.g., sequentially to increase the purity of variant strand isolation and/or to concentrate the variant strands after their subsequent removal from the capture primers, e.g., by heat denaturation).

Sorting Uniquely Tagged Nucleic Acids by Strand Displacement Synthesis

Strand displacement can also be used in conjunction with the subject invention as a way to sort and thus identify the tag sequence on uniquely tagged nucleic acids in a pooled sample (e.g., tagged with multiple sequence tokens, as described above).

We can look upon the displacement methods described below as specific extensions of chromatography. As in chromatography, the material to be fractionated, in this case a mixture of uniquely tagged nucleic acid molecules, is first bound to a solid support by hybridization to a universal capture oligonucleotide (i.e., an oligonucleotide that hybridizes to a sequence present in all nucleic acids in the sample). Differential elution of the nucleic acids by strand displacement can be achieved by exploiting the unique sequence tags. In the discussion below, we will use pins as the substrate configuration to demonstrate an exemplary method (but not the only method for) how the process may easily be automated. Pins can be constructed of any suitable material, e.g., one that is capable of capture primer or binding partner attachment and that will not interfere with the chemical and enzymatic reactions during processing, and are generally configured such that a leading end of the pin can be repeatedly inserted into reservoirs or wells containing a desired solution or other reagent (e.g., loading solutions, wash solutions, polymerization reagent pools, elution wells, etc.). In certain embodiments, pins are provided in one or two dimensional arrays to allow parallel processing (described below).

Figure 9:
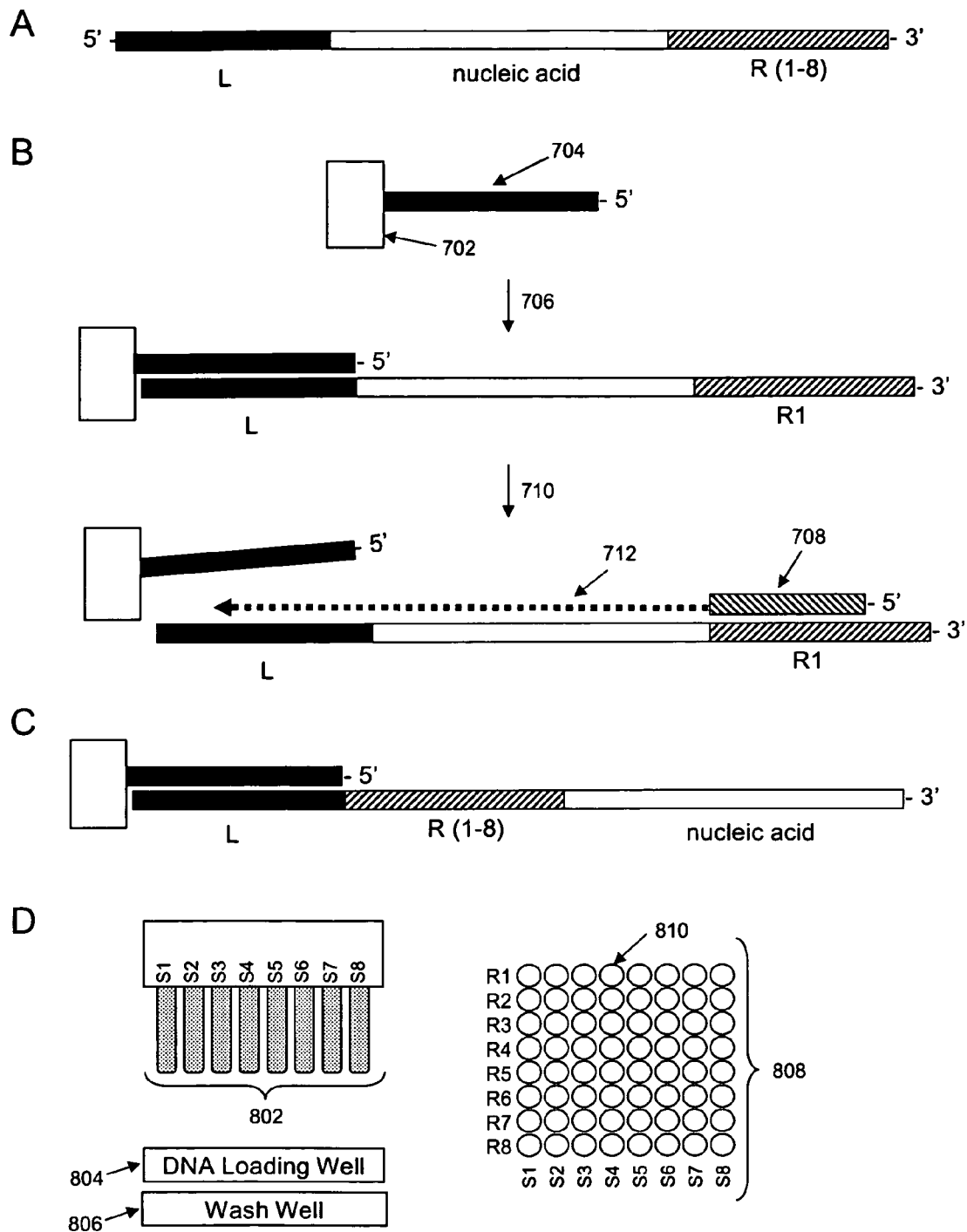
FIGS. 9A, 9B, 9C illustrate certain aspects of using strand displacement nucleic acid synthesis to sort a mixture differentially tagged nucleic acids according to the identity of their respective tags.
FIG. 9D illustrates an exemplary platform for using strand displacement nucleic acid synthesis to sort a mixture differentially tagged nucleic acids according to the identity of their respective tags.

For example, suppose we have a nucleic acid sample containing a mixture of nucleic acids each having ligated adapters, denoted as left and right (L and R (1-8); see FIG. 9A). For example, the sample may be a nucleic acid mixture containing tagged nucleic acids having a locus of interest from a number of different original samples, as described above. The L adapter is common between all nucleic acids in the sample while many different R adapters are employed as distinct tags for the nucleic acids being processed (selected from R1 to R8 in FIG. 9A). For example, the R adapters used can be a set of different sequence tokens, where each distinct sequence token denotes the original sample from which a nucleic acid insert is derived.

Each individual pin (702) used has attached thereto a capture primer (704) complementary to the common L adaptor, with the 3' end proximal to the pin (FIG. 9B). The DNA is rendered single stranded using any convenient method and hybridized to the capture primer (step 706) through the L adaptor. We now add a polymerization primer (708) to a particular R adaptor (R1 in FIG. 9B) followed by the addition of all 4 dNTPs and a strand-displacing polymerase (e.g., Bst DNA polymerase, Bca DNA polymerase, phi 29 DNA polymerase, etc.) (step 710). When the strand-displacing polymerase reaches the double-stranded region where the nucleic acid is hybridized to the capture primer, synthesis will continue and displace the capture primer from the nucleic acid that is bound to the solid surface (indicated by dotted arrow 712). This results in elution of nucleic acids that contain the specific R tag (i.e., the R1 tag complementary to the polymerization primer) from the pin into the solution phase. The pin, which still has single stranded molecules attached to it that were not primed with the anti-R1 oligonucleotide primer (i.e., nucleic acids that contain R tags that are not R1), can then be removed from the polymerization solution leaving the eluted nucleic acids behind. The pin can then be washed and primed with another R-specific polymerization primer (e.g., an anti-R2 primer in another well) and extended with a strand-displacing polymerase to elute another set of nucleic acids.

It is noted here that other tag configurations can be employed that are amenable to the above-described stranddisplacement-based sorting (it is not necessary to work with sequences at opposite ends of the molecules; see, e.g., the tag configuration in FIG. 9C).

Eluting polynucleotides by displacement can be used when the nucleic acids have been captured by oligonucleotide analogs, for example, peptide nucleic acids or others with different backbone structures (e.g., LNAs). Displacement elution also works when the base pairs formed are different, for example, Hoogsteen base pairs.

In certain embodiments, each nucleic acid in a sample is tagged with multiple distinct sequence tags (e.g., sequence tokens, as described above). Due to the presence of many specific, non-cross hybridizing binding regions in such embodiments, fractionating using strand displacement can attain a high level of specificity. Specifically, eluting tagged nucleic acids from the bound state according to their respective sequence tags can be achieved by iterative steps of: 1) adding a tag-specific oligonucleotide, and 2) nucleic acid synthesis with a strand-displacing polymerase. Unlike detaching the bound polynucleotides by heating, elution by displacement allows specific elution by many different specific oligonucleotides in a sequential manner.

Consider, for example, a mixture of uniquely tagged nucleic acids in which each tag is a distinct combination of two sequence tokens: one R tag selected from a group of 8 unique R tags and one S tag selected from a group of 8 unique S tags. This results in 64 possible unique combinations of token-tagged molecules (8R×8S=64 different R—S combinations). An example of a platform to perform the sorting of tagged nucleic acid samples based on these S and R tags is shown in FIG. 9D. In this figure, 8 different pins (802), each carrying an anti-S sequence (i.e., a capture primer complementary to one S sequence, denoted above each pin), are contacted to a tagged nucleic acid mixture in a DNA loading well (804) under hybridizing conditions to pick up molecules having their respective S tag (i.e., the first pin picks up S1-containing nucleic acids, the second pin picks up S2-containing nucleic acids, etc.). After hybridization has proceeded to completion, the pins are removed from the DNA loading well and washed in at least one wash well (806). Once washed, the pins are contacted sequentially to wells which each contain a single anti-R polymerization primer (R1 to R8) and eluted at each step by strand displacement as described above, with washing between each sequential contacting/eluting step. Array 808 shows an exemplary configuration of wells which each contain a single R-specific oligonucleotide primer (denoted at the left) which will be contacted sequentially with a single S pin (indicated at the bottom). In this manner, nucleic acids in the DNA sample in the DNA loading well are eluted into each well based on the cognate R—S designation (i.e., nucleic acids tagged with R1 and S4 are eluted from pin S4 into well R1, indicate at 810).

In certain embodiments, instead of transporting the pins physically, the solutions may be transported to the binding locations, e.g., in a microfluidic-based system.

The example above, shown for a linear array of pins (or comb) having distinct sequence token specificity, shows a two dimensional fractionation: a first fractionation in one dimension (i.e., on the S1 to S8 pins), followed by specific elution by distinct oligonucleotides in corresponding distinct wells in a second dimension (i.e., in the R1 to R8 wells). These dimensions can be expanded by increasing the total number of tokens used and/or the number of tokens that comprise each nucleic acid tag (whether a nucleic acid tag has 2, 3, 4, 5, 6, or more specific tokens).

For example, with 64 short token sequences used in pairs to tag nucleic acids, an implicit array of 32×32 can be designed to sort/separate 1024 DNAs (32×32=1024).

As described above, the use of oligonucleotides to 'capture' (e.g., oligonucleotide on a pin) followed by an 'eluting' (e.g., oligonucleotide primer for displacement synthesis) allows separation in two dimensions when nucleic acids have two distinct tags. When more tags are employed to tag nucleic acids, additional dimensions can be sorted using strand displacement elution.

For example, we can add in a third dimension by employing a third oligonucleotide complementary to a third tag on the nucleic acid (e.g., a Q tag) carrying a binding moiety (e.g., biotin) and then sequentially capturing these on an avidinylated support. The Q-captured nucleic acids can be eluted by displacement in a fourth dimension if need be (e.g., in the P dimension by eluting in distinct wells having specific P tag hybridizing oligonucleotides). This process can be thought of as converting a polymerization primer in one step to a capture primer in a subsequent step.

Based on the discussion above, there are numerous ways one could tag and sort a 4096 nucleic acid samples. For example, a mixture of distinctly tagged samples could be tagged either with two sets, each of 64 tokens (64 X and 64 Y), for a 2 dimensional separation, or with 3 sets of 16 tokens (16 K, 16 L and 16 M) for 3 dimensional separation, or with 4 sets of 8 tokens (8 P, 8 Q, 8 R and 8 S) for 4 dimensional separation (see Table 1 below).

TABLE 1

Sorting 4096 samples in different dimensions.

| Dimensionality | Capture | Displacement | Capture | Displacement |
|---|---|---|---|---|
| 2 Dimensions | X 64 | Y 64 | | |
| 3 Dimensions | K 16 | L 16 | M 16 | |
| 4 Dimensions | P 8 | Q 8 | R 8 | S 8 |

In certain embodiments, the third dimension can be achieved by adding a 2 dimensional array of pins (or brush) carrying the capture nucleotides. Thus the 4 dimensional separation is achieved by loading a comb of 8 P oligonucleotides, P1-P8, sequentially eluting into an 8×8 well array (or plate) with each row having one of the 8 Q oligonucleotides, Q1-Q8. Then 8 brushes carrying 64 pins coated with one of the R oligonucleotides R1-R8 are sequentially used to capture the corresponding polynucleotides in the third dimension. Each 64 pin brush is then sequentially eluted by displacement into 8 (64 well) plates in the 4th dimension, giving us 64 plates of 64 wells, and thus 4096 samples.

Figure 10:
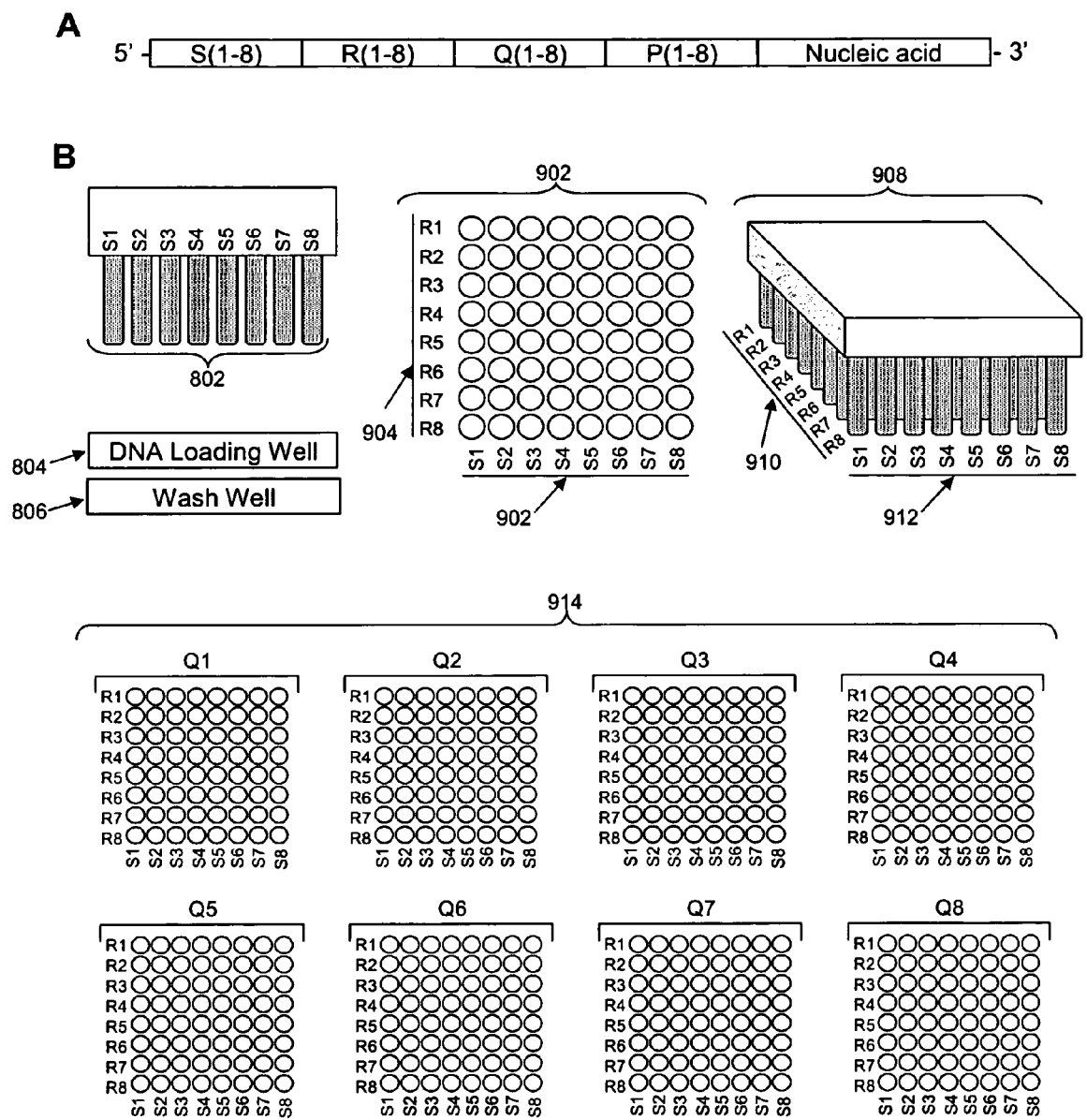
FIG. 10 illustrates another exemplary platform for using strand displacement nucleic acid synthesis to sort a mixture differentially tagged nucleic acids according to the identity of their respective tags.
Figure 11:
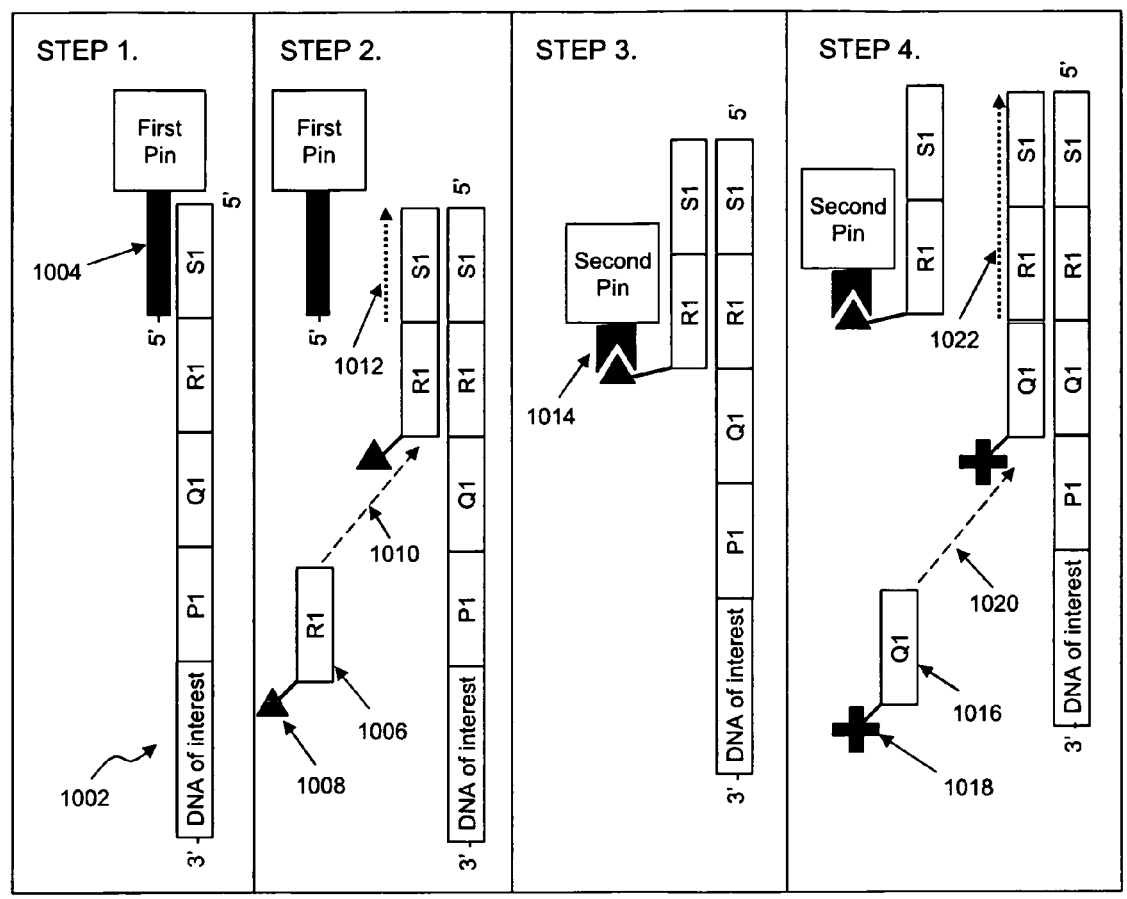
FIG. 11 illustrates one embodiment for sorting a nucleic acid having specific tags by strand displacement nucleic acid synthesis.

FIGS. 10 and 11 show another embodiment for dimensional sorting that employs binding moiety labeled oligonucleotides as elution primers. This embodiment is similar to that shown above, except that instead of immobilizing the nucleic acids to the solid surface using directly bound oligonucleotides, each eluting oligonucleotide is labeled with a binding moiety that is used to immobilize it to a substrate (having a corresponding binding partner) after it has been used as an elution primer. By alternating the identity of the binding moiety/binding partner pair, 4 dimensions or more can be sorted using strand displacement.

FIG. 10A shows the orientation of tags on a mixed nucleic acid sample being processed, where the tag orientation is sequential S, R, Q and P tags. FIG. 10B shows the first set of pins having attached S-specific capture oligonucleotides 802 (these are the same as shown in FIG. 9D). The pins are contacted to the mixed nucleic acid sample to be sorted in the DNA loading well 804 under hybridization conditions and washed at least once in wash well 806.

Once washed, the pins are contacted sequentially to an array of wells 902, each well having: the indicated R-specific primers 904, each of which are conjugated to a common first binding member (e.g., biotin); all 4 dNTPs; and a strand displacing polymerase under nucleic acid synthesis conditions (as described above). Each primer hybridizes to its cognate R site in the tagged nucleic acids, and the ensuing nucleic acid synthesis displaces the nucleic acids from the hybridizing S primer (906). Thus, nucleic acids having the specific S and R tag configuration are released into the designated well.

After the requisite 8 sequential steps of contacting/elution (i.e., the 8 S-pins are contacted to each of the R1 to R8 wells), an indexed array of 8×8 pins (also called a brush) having the binding partner of the first binding member bound thereto (908) is contacted to array 902 such that each indexed pin is contacted to its cognate well (the indexing is indicated on brush 908 at 910 and 912). This brush will pick up all DNAs in the 8×8 set of wells (902) by binding to the first binding member bound to the R-specific primer which is still hybridized to the DNA (and was extended through the S tag region).

The 8×8 brush is then transferred sequentially to 8, 8×8 arrays of wells (914), each 8×8 array of wells having: nucleic acid synthesis reagents, a strand displacing polymerase, and the a Q-specific primer coupled to a second binding member (i.e., one that does not bind to the binding partner of the first binding member) under nucleic acid synthesis conditions. The Q-specific primers hybridize to their cognate Q site in the tagged nucleic acids and the ensuing nucleic acid synthesis displaces nucleic acids from the indexed pin-bound R/S primer thus releasing nucleic acids having the specific Q tag.

In the next step (not shown), 8 indexed 8×8 brushes having the binding partner of second binding member will pick up all nucleic acids in each of the 8×8 arrays of wells of the Q set by binding to the second binding member on the primer (which is hybridized to the DNA). These indexed brushes (having a total of 512 distinct pins) are placed sequentially into 8 different arrays of 512 wells each containing nucleic acid synthesis reagents, a strand displacing polymerase, and a P specific primer conjugated to a third binding member (if further processing requires another binding member sorting step). Nucleic acid synthesis will elute any bound nucleic acid having the cognate P tag. In certain embodiments, the P-specific primers are conjugated to the first binding member as alternating between the first and second binding members/partners prevents erroneous binding of primers to pins in the wrong cycle.

The sorting steps for tags S, R and Q described above are shown in FIG. 11 for a nucleic acid having an S1-R1-Q1-P1 tag. In Step 1, the tagged nucleic acid being sorted (1002) hybridizes to anti-S1 oligonucleotide (1004) immobilized on the first pin. In Step 2, the first pin is placed into a well having an R1-specific primer (1006) with a first binding member (1008) which hybridizes to its cognate R1 site in the nucleic acid (1010). Strand displacement synthesis (1012) elutes the nucleic acid strand into the solution phase and the first pin is removed from the solution (not shown). In Step 3, the sample is contacted to a second pin having a binding member for first binding moiety immobilized thereon (1014), which serves to immobilize the nucleic acids in the well to the second pin. In Step 4, the second pin is placed into a well containing a Q1-specific oligonucleotide primer (1016) with a second binding moiety (1018) where the Q1-specific oligonucleotide primer hybridizes to the Q1 tag in the nucleic acid being sorted (1020). Strand displacement synthesis (1022) elutes the S1-R1-Q1 tagged nucleic acid strand into the solution phase. In a subsequent step (not shown), the eluted nucleic acid from Step 4 is bound to a third pin having a binding member for the second binding moiety immobilized thereon (similar to in Step 3). This pin is then placed into a well with a P1-specific oligonucleotide primer and eluted as described for Step 4. As indicated above in describing FIG. 9, the P1 oligonucleotide may be tagged with a third binding moiety (or the first binding moiety) if desired to facilitate further downstream processing.

We can adjust the stability of each of tag/oligonucleotide hybrid formed by adjusting the length of the tag and/or the oligonucleotide sequence as well as by its composition. If we keep the volumes in each well small, the hybridizations will be essentially instantaneous, and because nucleic acid synthesis is rapid, this process should not take long periods of time. The resulting eluted DNA can be easily manipulated (e.g., amplified by PCR, cloned, sequenced, etc.). RNA can also be used as a template, because reverse transcriptase (RT) is a strand displacing polymerase.

Identification of Uniquely Tagged Nucleic Acid Isolates Using Microfluidic System The specific configuration of the tags on the nucleic acids being analyzed can be designed to be used with any of a variety of tag detection systems. The following example employs tags having two dimensions (or subunits) in a microfluidics-based detection system.

In this example, a set of unique nucleic acid tags is generated having a first subunit selected from a first set of four A tags and a second subunit selected from a set of 256 B tags. This configuration provides for the generation of 1024 distinct tags (4×256=1024), and thus can be employed in assays processing nucleic acid samples that include nucleic acids derived from up to 1024 distinct sources (or individuals).

Figure 12:
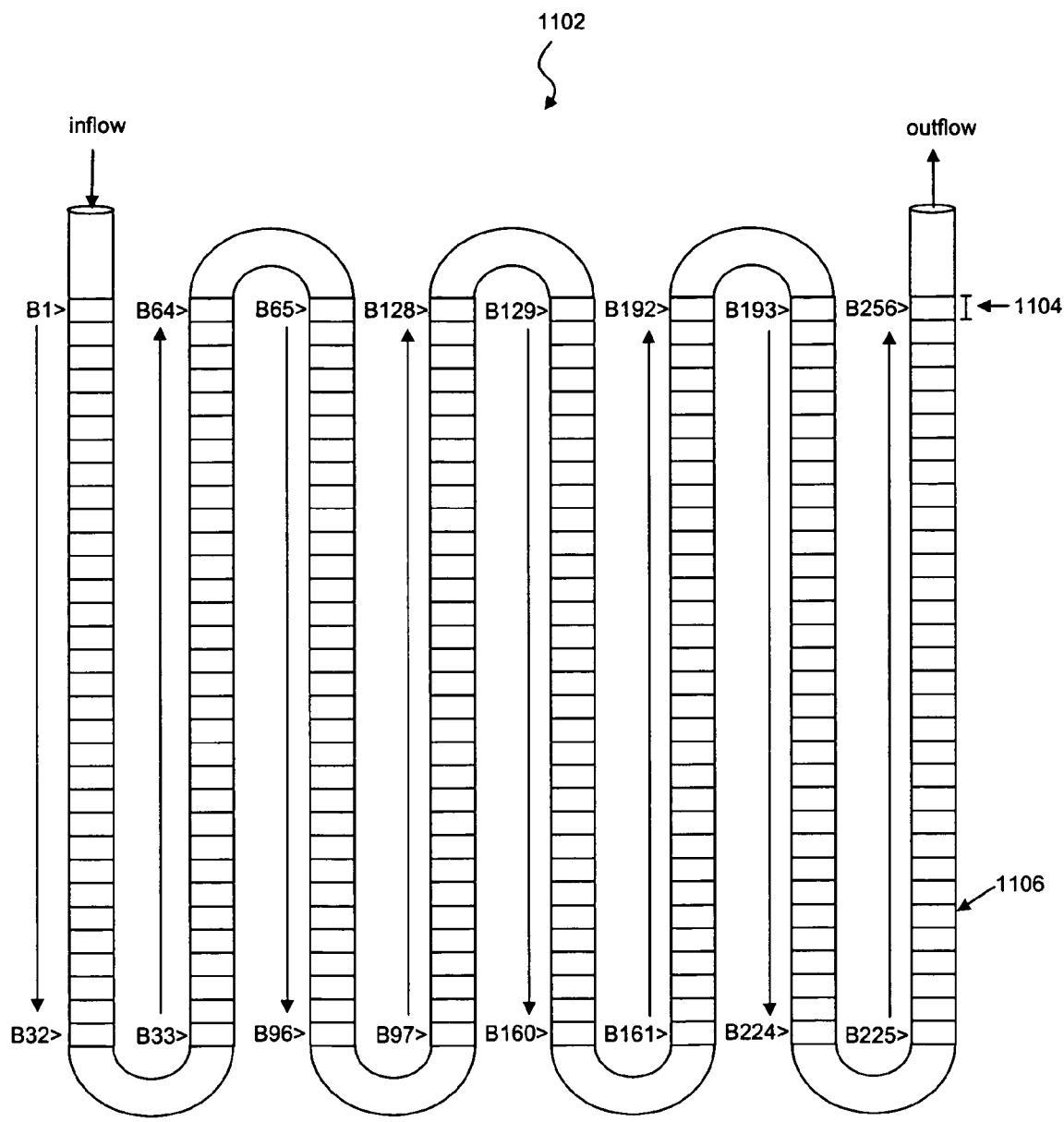
FIG. 12 illustrates an exemplary microfluidic platform for decoding a mixture of nucleic acids which are tagged with a unique combination of A subunit and B subunit tags.

The microfluidic system includes an immobilized ladder of 256 anti-B subunit oligonucleotide tags embedded in a channel at approximately 100 micron intervals. This results in a channel of about 2.56 centimeters (cm) in length (about 1 inch). The anti-B tags in the channel will specifically hybridize to cognate tags in nucleic acids flowed therethrough (i.e., under appropriately stringent hybridization conditions). In FIG. 12, microfluidic channel 1102 is shown as a serpentine structure having 8 segments, with each segment having 32 anti-B subunit oligonucleotide tags embedded therein at 100 micron intervals (104) for a total of 256 anti-B tag regions. The starting and ending anti-B oligonucleotide tag for each segment are indicated to the left (numbered according to its cognate B-tag, in increasing order). Each distinct region in each channel has a distinct anti-B oligonucleotide tag and is indicated by a box (e.g., box 1106 represents the location in the channel where the anti-B230 oligonucleotide is immobilized). The arrows indicate the direction of flow through the channel, with inflow and outflow indicated. The channel configuration and dimensionality described herein are merely exemplary, as microfluidic systems having different dimensions can be employed.

After isolation of nucleic acids according to the subject invention, they are processed and applied to the microfluidic device to determine the identity of their tags. The processing involves contacting the nucleic acids under hybridization conditions to four anti-A tags, each of which includes a distinguishing detectable label. For example, the four A tags may each have a different fluorescent label that can be distinguished from each other upon detection (e.g., FITC, PE, APC and Texas Red). The four anti-A tags will hybridize to their cognate tags in the nucleic acids, thereby labeling each of the isolated nucleic acids with a single distinguishing label such that all nucleic acids having a first A tag will be labeled with a first label, all nucleic acids having a second A tag will be labeled with a second label, all nucleic acids having a third A tag will be labeled with a third label, and all nucleic acids having a fourth A tag will be labeled with a fourth label.

These labeled nucleic acids are then applied to the microfluidic channel under conditions where their B subunit tags will hybridize to their cognate anti-B tags immobilized within the microfluidic channel. This will lead to a spatial distribution of nucleic acids within the channel, with nucleic acids having a specific B tag co-localizing to the location in the microfluidic channel where its cognate anti-B tag resides. Because the nucleic acids have been detectibly tagged according to the identity of their A tag region, detection of a specific detectable moiety at a specific location in the microfluidic channel reveals the identity of all tags present in the isolated sample. From this, the origin of each of the isolated nucleic acids can be deduced (because each nucleic acid carries a tag identifying from which original sample from which it was derived).

In certain embodiments, the isolated nucleic acids are amplified prior to decoding their identification tags, e.g., linearly using RNA polymerase, as described above.

It is to be understood here that the description above is merely exemplary, as many alternative configurations for labeling and detecting nucleic acids to decode their unique tags are made apparent from the description above. For example, as there exist a wide variety of different distinguishable detectable moieties (e.g., fluorescent moieties), it is clear that one can employ many more than the four different A tags in the embodiment described above.

Kits and Systems

Also provided by the subject invention are kits and systems for practicing the subject methods, as described above, such as combs having an array of immobilized oligonucleotides specific for a nucleic acid having a locus of interest. In some embodiments, systems and kits contain programming means to allow a robotic system to perform the subject methods, e.g., programming for instructing a robotic pipettor to add, mix and remove reagents in accordance with one or more reference sequences, as described above. Systems may include robotic components for carrying out one or more of the steps of the subject methods and be configured for use with the subject kits (described below). The various components of the kits may be present in separate containers or certain compatible components may be precombined into a single container, as desired.

The subject systems and kits may also include one or more other reagents for preparing or processing a nucleic acid sample according to the subject methods (e.g., polymerization reagent pool sets, unique tagging reagents, displacement synthesis reagents [e.g., multi-well plates having specific arrangement of displacement oligos], solid immobilization surfaces, e.g., combs, pins, etc.). The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a nucleic acid variant isolation assay according to the present invention.

In addition to above-mentioned components, the subject kits typically further include instructions for using the components of the kit to practice the subject methods, e.g., to isolate a nucleic acid having a sequence variation as compared to a reference sequence according to the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control analyte mixtures, e.g., two or more control samples for use in testing the kit.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

That which is claimed is:

1. A method of sorting nucleic acid molecules according to the identity of their corresponding unique nucleotide tags, said method comprising:
   (i) contacting a nucleic acid sample comprising at least two nucleic acid molecules each having a unique tag to a capture primer under hybridization conditions, wherein said capture primer is immobilized on a substrate and comprises a sequence complementary to a capture primer binding site in said at least two nucleic acid molecules, whereby said at least two nucleic acid molecules are immobilized;
   (ii) contacting said immobilized at least two nucleic acid molecules to a polymerization primer under hybridization conditions, wherein said polymerization primer comprises a sequence complementary to all of or a region in the unique tag of a first of said at least two nucleic acid molecules, wherein said polymerization primer binds to the same strand of said first nucleic acid molecules as said capture primer at a location that is 5' to said capture primer; and
   (iii) isolating said first nucleic acid molecules by contacting said immobilized at least two nucleic acid molecules to a displacing nucleotide polymerase under nucleic acid polymerization conditions, wherein extension of said polymerization primer displaces said first nucleic acid molecules from said immobilized capture primer;
   wherein said at least two uniquely-tagged nucleic acid molecules are sorted according to the identity of their corresponding unique nucleotide tags.

2. The method of claim 1, wherein said method further comprises isolating a second of said at least two nucleic acid molecules by repeating steps (ii) and (iii) using a second polymerization primer, wherein said second polymerization primer comprises a sequence complementary to all of or a region in the unique tag of said second nucleic acid molecules, wherein said second polymerization primer binds to the same strand of said second nucleic acid molecules as said capture primer at a location that is 5' to said capture primer.

3. The method of claim 1, wherein said substrate is a pin.

4. The method of claim 1, wherein said capture primer is immobilized on said substrate via interaction between a binding moiety on said capture primer and a binding partner specific for said binding moiety on said substrate.

5. The method of claim 4, wherein said binding moiety is biotin.

6. The method of claim 1, wherein said at least two nucleic acid molecules have different origins.

7. The method of claim 6, wherein said unique tag denotes the origin of each of said at least two nucleic acid molecules.

8. The method of claim 1, wherein said unique tag of said at least two nucleic acid molecules comprises multiple distinct regions, wherein said multiple distinct regions are non-cross hybridizing regions.

9. The method of claim 8, wherein each of said multiple distinct regions comprises a sequence token tag.

10. The method of claim 8, wherein said isolated first nucleic acid molecules of step (iii) are subjected to a second round of sorting according to the identity of a second of said multiple distinct regions in said unique tag.

11. The method of claim 10, wherein the polymerization primer employed in step (ii) for the first round of sorting comprises a binding moiety, wherein step (i) of the second round of sorting comprises contacting the isolated first nucleic acid molecules of step (iii) in the first round of sorting to a second substrate having immobilized thereon corresponding binding partners of said binding moiety to immobilize said isolated first nucleic acid molecules, thereby converting the polymerization primer in the first round of sorting to the capture primer in the second round of sorting.

12. The method of claim 8, wherein said isolated first nucleic acid molecules of step (iii) are subjected to iterative rounds of sorting according to the identity of each of said multiple distinct regions in said unique tag.

13. The method of claim 12, wherein the polymerization primer employed in step (ii) for a prior round of sorting comprises a binding moiety, wherein step (i) in the subsequent round of sorting comprises contacting the isolated nucleic acid molecules of step (iii) in the prior round of sorting to a substrate having immobilized thereon corresponding binding partners of said binding moiety to immobilize said isolated nucleic acid molecules, thereby converting the polymerization primer in a prior round of sorting to the capture primer in a subsequent round of sorting.

14. The method of claim 8, wherein said capture primer is specific for a first of said multiple distinct regions in said unique tag.

15. The method of claim 8, wherein step (i) further comprises employing multiple capture primers immobilized on separate substrates, wherein each of said multiple capture primers is specific for a corresponding first of said multiple distinct regions in said at least two nucleic acid molecules.

16. The method of claim 15, wherein the polymerization primer employed in step (ii) is identical for each of said multiple capture primers.

17. The method of claim 15, wherein said multiple capture primers are immobilized on different pins of a comb.

18. The method of claim 15, wherein said multiple capture primers are immobilized on different pins of a brush.

19. A method of sorting nucleic acid molecules according to the presence of a unique nucleotide sequence, said method comprising:
  (i) contacting a nucleic acid sample comprising at least two nucleic acid molecules to a capture primer under hybridization conditions, wherein said capture primer is immobilized on a substrate and comprises a sequence complementary to a capture primer binding site present in said at least two nucleic acid molecules, whereby said at least two nucleic acid molecules are immobilized;
  (ii) contacting said immobilized at least two nucleic acid molecules to a polymerization primer under hybridization conditions, wherein said polymerization primer comprises a sequence complementary to a unique sequence present in a first of said at least two nucleic acid molecules, wherein said polymerization primer binds to the same strand of said first nucleic acid molecules as said capture primer at a location that is 5' to said capture primer; and
  (iii) isolating said first nucleic acid molecules by contacting said immobilized at least two nucleic acid molecules to a displacing nucleotide polymerase under nucleic acid polymerization conditions, wherein extension of said polymerization primer displaces said first nucleic acid molecules from said immobilized capture primer;
  wherein said nucleic acid molecules are sorted according to the presence of said unique sequence.

20. The method of claim 19, wherein said method further comprises isolating a second of said at least two nucleic acid molecules by repeating steps (ii) and (iii) using a second polymerization primer, wherein said second polymerization primer comprises a sequence complementary to a second unique sequence present in said second nucleic acid molecules, wherein said second polymerization primer binds to the same strand of said second nucleic acid molecules as said capture primer at a location that is 5' to said capture primer.

\* \* \* \* \*

UNITED STATES PATENT AND TRADEMARK OFFICE
CERTIFICATE OF CORRECTION

PATENT NO.       : 7,635,566 B2                                Page 1 of 1
APPLICATION NO.  : 12/163571
DATED            : December 22, 2009
INVENTOR(S)      : Sydney Brenner It is certified that error appears in the above-identified patent and that said Letters Patent is hereby corrected as shown below:

In Column 18, line 67, replace the following sequence of letters:
"RAGATCY" with R^GATCY

In Column 19, line 4, replace the following sequence of letters:
"AGATC" with ^GATC

Signed and Sealed this

First Day of June, 2010

David J. Kappos
*Director of the United States Patent and Trademark Office*